(12) United States Patent
Yahiaoui et al.

(10) Patent No.: US 10,022,468 B2
(45) Date of Patent: Jul. 17, 2018

(54) ABSORBENT ARTICLES CONTAINING A MULTIFUNCTIONAL GEL

(75) Inventors: Ali Yahiaoui, Roswell, GA (US); Candace Dyan Krautkramer, Neenah, WI (US); Margaret Gwyn Latimer, Alpharetta, GA (US); Jack Nelson Lindon, Alpharetta, GA (US); Russell F. Ross, Atlanta, GA (US); Melissa Jean Dennis, Appleton, WI (US); Garry Roland Woltman, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1331 days.

(21) Appl. No.: 12/364,365

(22) Filed: Feb. 2, 2009

(65) Prior Publication Data

US 2010/0198177 A1 Aug. 5, 2010

(51) Int. Cl.
*A61F 13/53* (2006.01)
*A61F 13/82* (2006.01)
*A61L 15/58* (2006.01)
*A61L 15/60* (2006.01)

(52) U.S. Cl.
CPC .............. *A61L 15/58* (2013.01); *A61F 13/82* (2013.01); *A61L 15/60* (2013.01); *A61F 2013/530481* (2013.01)

(58) Field of Classification Search
CPC .......... A61F 13/53; A61F 13/82; A61L 15/58; A61L 15/60
USPC ......................................... 604/359, 367, 368
See application file for complete search history.

(56) References Cited

U.S. PATENT DOCUMENTS

| | | | |
|---|---|---|---|
| 2,842,897 A | 7/1958 | Finn | |
| 3,288,346 A | 11/1966 | Peppler | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |

(Continued)

FOREIGN PATENT DOCUMENTS

| | | |
|---|---|---|
| DE | 69232589 T2 | 12/2002 |
| EP | 0353972 | 2/1990 |

(Continued)

OTHER PUBLICATIONS

Jillian Lloyd, Naomi Crouch, Catherine Minto, Lih-Mei Liao, Sarah Creighton, Female Genital Appearance: 'Normality' Unfolds, BJOG: An International Journal of Obstetrics and Gynecology, May 2005, vol. 112, pp. 643-646, Blackwell Publishing.

(Continued)

*Primary Examiner* — Kathryn E Ditmer
(74) *Attorney, Agent, or Firm* — Armstrong Teasdale LLP

(57) ABSTRACT

Improved skin-adhesive compositions for bonding a substrate, such as an absorbent article, to skin are disclosed. More particularly, the skin-adhesive composition has an improved, yet gentle, adhesion to the skin of a user, while maintaining strong, effective bonding to various inanimate, non-skin substrates. In one embodiment, the skin-adhesive composition can provide one or more skin benefit agents to the user. The skin-adhesive composition may be applied to an absorbent article, such as a panty-liner, sanitary napkin, or an incontinence article, for directly adhering the article to the skin of a user.

12 Claims, 5 Drawing Sheets

(56) References Cited

U.S. PATENT DOCUMENTS

| | | | |
|---|---|---|---|
| 3,542,615 A | 11/1970 | Dobo et al. | |
| 3,598,123 A | 8/1971 | Zaffaroni | |
| 3,692,618 A | 9/1972 | Dorschner et al. | |
| 3,731,683 A | 5/1973 | Zaffaroni | |
| 3,802,817 A | 4/1974 | Matsuki et al. | |
| 3,849,241 A | 11/1974 | Butin et al. | |
| 3,963,029 A | 6/1976 | Brooks | |
| 3,972,328 A | 8/1976 | Chen | |
| 3,998,215 A * | 12/1976 | Anderson et al. | 600/397 |
| 4,072,151 A | 2/1978 | Levine | |
| 4,340,563 A | 7/1982 | Appel et al. | |
| 4,488,928 A | 12/1984 | Ali Khan et al. | |
| 4,505,976 A | 3/1985 | Doehnert et al. | |
| 4,556,056 A * | 12/1985 | Fischer et al. | 604/304 |
| 4,631,062 A | 12/1986 | Lassen et al. | |
| 4,673,403 A | 6/1987 | Lassen et al. | |
| 4,743,245 A | 5/1988 | Lassen et al. | |
| 4,758,241 A | 7/1988 | Papajohn | |
| 4,781,712 A | 11/1988 | Barabino et al. | |
| 4,798,603 A | 1/1989 | Meyer et al. | |
| 4,804,380 A | 2/1989 | Lassen et al. | |
| 4,846,824 A | 7/1989 | Lassen et al. | |
| 4,909,244 A * | 3/1990 | Quarfoot et al. | 602/48 |
| 4,977,892 A * | 12/1990 | Ewall | 602/52 |
| 5,051,259 A | 9/1991 | Olsen et al. | |
| 5,114,419 A | 5/1992 | Daniel et al. | |
| 5,133,705 A | 7/1992 | Nakanishi et al. | |
| 5,147,938 A | 9/1992 | Kuller | |
| 5,160,328 A * | 11/1992 | Cartmell et al. | 604/307 |
| 5,194,299 A | 3/1993 | Fry | |
| 5,194,550 A | 3/1993 | Rance et al. | |
| 5,221,275 A | 6/1993 | Van Iten | |
| 5,277,954 A | 1/1994 | Carpenter et al. | |
| 5,369,155 A | 11/1994 | Asmus | |
| 5,382,400 A | 1/1995 | Pike et al. | |
| 5,387,208 A | 2/1995 | Ashton et al. | |
| 5,419,956 A | 5/1995 | Roe | |
| 5,445,627 A | 8/1995 | Mizutani et al. | |
| 5,554,381 A | 9/1996 | Roos et al. | |
| H1602 H | 10/1996 | Brock | |
| 5,591,146 A | 1/1997 | Hasse | |
| 5,599,335 A | 2/1997 | Goldman et al. | |
| 5,611,790 A | 3/1997 | Osborn, III et al. | |
| 5,614,310 A | 3/1997 | Delgado et al. | |
| 5,618,281 A | 4/1997 | Betrabet et al. | |
| 5,618,282 A | 4/1997 | Schlangen | |
| 5,632,736 A | 5/1997 | Block | |
| 5,658,270 A | 8/1997 | Lichstein | |
| 5,662,633 A | 9/1997 | Doak et al. | |
| 5,669,894 A | 9/1997 | Goldman et al. | |
| 5,706,950 A | 1/1998 | Houghton et al. | |
| 5,714,225 A | 2/1998 | Hansen et al. | |
| 5,716,621 A | 2/1998 | Bello et al. | |
| 5,759,560 A | 6/1998 | Dillon | |
| 5,769,837 A | 6/1998 | Parr | |
| 5,800,417 A | 9/1998 | Goerg-Wood et al. | |
| 5,807,367 A | 9/1998 | Dilnik et al. | |
| 5,811,116 A | 9/1998 | Gilman et al. | |
| 5,830,202 A | 11/1998 | Bogdanski et al. | |
| 5,885,265 A | 3/1999 | Osborn, III et al. | |
| 5,897,546 A | 4/1999 | Kido et al. | |
| 5,910,125 A | 6/1999 | Cummings et al. | |
| 5,994,613 A | 11/1999 | Cummings et al. | |
| 6,045,900 A | 4/2000 | Haffner et al. | |
| 6,155,265 A | 12/2000 | Hammerslag | |
| 6,156,818 A | 12/2000 | Corzani et al. | |
| 6,177,482 B1 | 1/2001 | Cinelli et al. | |
| 6,187,989 B1 | 2/2001 | Corzani et al. | |
| 6,191,189 B1 | 2/2001 | Cinelli et al. | |
| 6,211,263 B1 | 4/2001 | Cinelli et al. | |
| 6,213,993 B1 | 4/2001 | Zacharias et al. | |
| 6,255,552 B1 | 7/2001 | Cummings et al. | |
| 6,316,524 B1 | 11/2001 | Corzani et al. | |
| 6,336,935 B1 | 1/2002 | Davis et al. | |
| 6,362,389 B1 | 3/2002 | McDowall et al. | |
| 6,365,645 B1 | 4/2002 | Cinelli et al. | |
| 6,369,126 B1 | 4/2002 | Cinelli et al. | |
| 6,386,203 B1 | 5/2002 | Hammerslag | |
| 6,479,724 B1 * | 11/2002 | Areskoug et al. | 602/41 |
| 6,491,953 B1 | 12/2002 | Sojka et al. | |
| 6,495,229 B1 | 12/2002 | Carte et al. | |
| 6,565,961 B2 | 5/2003 | Koslow | |
| 6,566,575 B1 | 5/2003 | Stickels et al. | |
| 6,582,411 B1 | 6/2003 | Carstens et al. | |
| 6,613,030 B1 | 9/2003 | Coles et al. | |
| 6,613,955 B1 | 9/2003 | Lindsay et al. | |
| 6,616,643 B1 | 9/2003 | Costa | |
| 6,617,490 B1 | 9/2003 | Chen et al. | |
| 6,620,143 B1 | 9/2003 | Zacharias et al. | |
| 6,632,210 B1 | 10/2003 | Glasgow et al. | |
| 6,641,569 B1 | 11/2003 | Coles et al. | |
| 6,657,009 B2 | 12/2003 | Zhou | |
| 6,670,402 B1 | 12/2003 | Lee et al. | |
| 6,683,143 B1 * | 1/2004 | Mumick et al. | 526/240 |
| 6,733,483 B2 | 5/2004 | Raufman et al. | |
| 6,756,520 B1 | 6/2004 | Krzysik et al. | |
| 6,803,420 B2 * | 10/2004 | Cleary et al. | 525/205 |
| 6,997,915 B2 | 2/2006 | Gell et al. | |
| 7,033,342 B2 | 4/2006 | Mizutani et al. | |
| 7,045,559 B2 | 5/2006 | Yahiaoui et al. | |
| 7,053,131 B2 | 5/2006 | Ko et al. | |
| 7,063,859 B1 | 6/2006 | Kanios et al. | |
| 7,122,022 B2 | 10/2006 | Drevik | |
| 7,125,401 B2 | 10/2006 | Yoshimasa | |
| 7,198,689 B2 | 4/2007 | Van Gompel et al. | |
| 7,217,259 B2 | 5/2007 | McDaniel | |
| 7,265,158 B2 | 9/2007 | Risen, Jr. et al. | |
| 7,358,282 B2 | 4/2008 | Krueger et al. | |
| 7,378,450 B2 | 5/2008 | Erkey et al. | |
| 7,468,205 B2 | 12/2008 | Schwertfeger et al. | |
| 7,918,837 B2 | 4/2011 | Rosenfeld | |
| 2001/0039407 A1 | 11/2001 | Widlund | |
| 2002/0013566 A1 | 1/2002 | Chappell et al. | |
| 2002/0037977 A1 | 3/2002 | Feldstein et al. | |
| 2002/0193766 A1 | 12/2002 | Gell et al. | |
| 2003/0004484 A1 | 1/2003 | Hammons et al. | |
| 2003/0065302 A1 | 4/2003 | Kuroda et al. | |
| 2003/0065304 A1 | 4/2003 | Bernhard et al. | |
| 2003/0078554 A1 | 4/2003 | Drevik | |
| 2003/0106825 A1 | 6/2003 | Molina et al. | |
| 2003/0170308 A1 * | 9/2003 | Cleary et al. | 424/486 |
| 2003/0203011 A1 * | 10/2003 | Abuelyaman et al. | 424/445 |
| 2003/0208112 A1 | 11/2003 | Schmidt et al. | |
| 2003/0212416 A1 | 11/2003 | Cinelli et al. | |
| 2004/0005830 A1 | 1/2004 | Anderson et al. | |
| 2004/0059310 A1 | 3/2004 | Gagliardi et al. | |
| 2004/0115251 A1 | 6/2004 | Goldman et al. | |
| 2004/0116883 A1 | 6/2004 | Krautkramer et al. | |
| 2004/0122385 A1 | 6/2004 | Morman et al. | |
| 2004/0133143 A1 | 7/2004 | Burton et al. | |
| 2004/0151930 A1 | 8/2004 | Rouns et al. | |
| 2004/0158221 A1 | 8/2004 | Mizutani et al. | |
| 2004/0167488 A1 | 8/2004 | Bellucci et al. | |
| 2004/0167491 A1 | 8/2004 | Mizutani | |
| 2004/0209075 A1 | 10/2004 | Maloney | |
| 2005/0010185 A1 | 1/2005 | Mizutani et al. | |
| 2005/0014901 A1 | 1/2005 | Osae et al. | |
| 2005/0036957 A1 | 2/2005 | Prencipe et al. | |
| 2005/0059918 A1 * | 3/2005 | Sigurjonsson et al. | 602/54 |
| 2005/0124960 A1 | 6/2005 | Ruman | |
| 2005/0136023 A1 * | 6/2005 | Yahiaoui et al. | 424/70.13 |
| 2005/0136077 A1 * | 6/2005 | Yahiaoui et al. | 424/401 |
| 2005/0137549 A1 | 6/2005 | Lindsay et al. | |
| 2005/0148984 A1 | 7/2005 | Lindsay et al. | |
| 2005/0182378 A1 | 8/2005 | Bonelli et al. | |
| 2005/0226917 A1 * | 10/2005 | Burton | 424/445 |
| 2005/0233149 A1 | 10/2005 | Ansell | |
| 2005/0244442 A1 | 11/2005 | Sabino et al. | |
| 2005/0261652 A1 | 11/2005 | Digiacomantonio et al. | |
| 2006/0058760 A1 | 3/2006 | Rosenfeld et al. | |
| 2006/0058764 A1 | 3/2006 | Bohlen et al. | |
| 2006/0063322 A1 | 3/2006 | Hsu et al. | |
| 2006/0129114 A1 | 6/2006 | Mason, Jr. et al. | |
| 2006/0142722 A1 | 6/2006 | Koenig et al. | |

(56) References Cited

U.S. PATENT DOCUMENTS

| | | | |
|---|---|---|---|
| 2006/0148352 A1* | 7/2006 | Munro et al. | 442/118 |
| 2006/0148917 A1 | 7/2006 | Radwanski et al. | |
| 2006/0161125 A1 | 7/2006 | Bohlen et al. | |
| 2006/0188940 A1 | 8/2006 | Cima et al. | |
| 2006/0195053 A1 | 8/2006 | Oelund et al. | |
| 2006/0205835 A1 | 9/2006 | Husemann et al. | |
| 2006/0206077 A1 | 9/2006 | Warren et al. | |
| 2006/0216523 A1 | 9/2006 | Takai | |
| 2006/0224133 A1 | 10/2006 | Gannon et al. | |
| 2006/0224134 A1 | 10/2006 | Luizzi et al. | |
| 2006/0240087 A1 | 10/2006 | Houze et al. | |
| 2006/0258788 A1 | 11/2006 | Coggins et al. | |
| 2006/0264884 A1 | 11/2006 | Carstens | |
| 2007/0031463 A1 | 2/2007 | Fotinos et al. | |
| 2007/0100313 A1 | 5/2007 | Luizzi | |
| 2007/0124850 A1 | 6/2007 | Buettner | |
| 2007/0250028 A1 | 10/2007 | Woltman et al. | |
| 2007/0275068 A1 | 11/2007 | Martens et al. | |
| 2007/0287973 A1 | 12/2007 | Cohen et al. | |
| 2008/0015535 A1 | 1/2008 | Gannon et al. | |
| 2008/0057811 A1 | 3/2008 | Yahiaoui et al. | |
| 2008/0071237 A1 | 3/2008 | Chen et al. | |
| 2008/0147035 A1 | 6/2008 | Snell | |
| 2008/0161492 A1 | 7/2008 | Cleary et al. | |
| 2008/0207779 A1 | 8/2008 | Yahiaoui et al. | |
| 2008/0234647 A1 | 9/2008 | Arterburn | |
| 2009/0062761 A1 | 3/2009 | Goerg-Wood et al. | |
| 2009/0071862 A2 | 3/2009 | Snell | |
| 2010/0121304 A1 | 5/2010 | Zhou et al. | |
| 2011/0092945 A1 | 4/2011 | Carstens | |
| 2011/0135726 A1* | 6/2011 | Munro et al. | 424/484 |

FOREIGN PATENT DOCUMENTS

| | | |
|---|---|---|
| EP | 0638303 | 11/1997 |
| EP | 0850628 | 7/1998 |
| EP | 909662 A2 | 4/1999 |
| EP | 0609236 B1 | 5/2002 |
| EP | 1407737 A1 | 4/2004 |
| EP | 1468661 | 10/2004 |
| EP | 1649873 A2 | 4/2006 |
| EP | 1407743 B1 | 1/2010 |
| GB | 2284767 | 6/1995 |
| JP | 04279159 | 10/1992 |
| JP | 9117473 A | 5/1997 |
| KR | 1020010022000 A | 3/2001 |
| KR | 100563880 B1 | 3/2006 |
| RU | 2276998 | 5/2006 |
| RU | 2277891 | 6/2006 |
| RU | 2286801 C2 | 11/2006 |
| WO | 1993007841 A1 | 4/1993 |
| WO | 95016424 | 6/1995 |
| WO | 98027910 | 7/1998 |
| WO | 98027912 | 7/1998 |
| WO | 98027913 | 7/1998 |
| WO | 98027915 | 7/1998 |
| WO | 98027916 | 7/1998 |
| WO | 98027917 | 7/1998 |
| WO | 98027918 | 7/1998 |
| WO | 98028015 | 7/1998 |
| WO | 98028017 | 7/1998 |
| WO | 98028019 | 7/1998 |
| WO | 98028022 | 7/1998 |
| WO | 98028023 | 7/1998 |
| WO | 9847454 A1 | 10/1998 |
| WO | 9857609 A1 | 12/1998 |
| WO | 98055065 | 12/1998 |
| WO | 99001094 | 1/1999 |
| WO | 99001095 | 1/1999 |
| WO | 9930659 A1 | 6/1999 |
| WO | 2000000235 | 1/2000 |
| WO | 0126595 A1 | 4/2001 |
| WO | 2002087642 A2 | 5/2002 |
| WO | 02087645 A1 | 11/2002 |
| WO | 2006062343 A1 | 7/2003 |
| WO | 200493766 A1 | 11/2004 |
| WO | 2006028612 | 3/2006 |
| WO | 2010077306 A1 | 7/2010 |

OTHER PUBLICATIONS

Final Rule for U.S. Antiperspirant Drug Products for Over-the-Counter Human Use; Final Monograph, vol. 68, No. 110 Fed. Reg. 34273-34293 (Jun. 9, 2003).

Berner et al., Photo Initiators—An Overview, J. Radiation Curing (Apr. 1979), pp. 29.

Mandavi et al., A Biodegradable and Biocompatible Gecko-inspired Tissue Adhesive, PNAS, vol. 105: 7, pp. 2307-2312.

American Society for Testing Materials (ASTM) Designation: D1300-53 T, "Tentative Specifications and Methods of Test for Laminated Thermosetting Decorative Sheets," pp. 148-166, issued 1953.

International Search Report & Written Opinion for PCT/IB32010/050416, dated Nov. 1, 2010.

Office Action received in EP Application U.S. Appl. No. 04750195.2 dated Jul. 6, 2010.

Non-final Office Action received in U.S. Appl. No. 12/364,421 dated Sep. 6, 2011.

Matsumoto; "Characteristic polymerization behaviour of microgel-like poly(allyl methacrylate) microspheres"; Macromolecular Symposia; 2002; pp. 141-152; vol. 179, No. 1.

Supplemental European Search Report from EP Application No. 08789525.6 dated Sep. 21, 2012.

International Search Report for PCT/IB2009/053073 dated Mar. 26, 2010; 13 pages.

International Search Report for PCT/IB2009/053074 dated Mar. 26, 2010; 11 pages.

International Search Report for PCT/IB32010/050407 dated Oct. 21, 2010; 10 pages.

International Search Report for PCT/IB2009/054647 dated May 31, 2010; 12 pages.

Translation of Russian Patent Examination Report for Patent Application No. 2011123315, dated Feb. 25, 2013; 3 pages.

Chinese First Office Action for Patent Application No. 201080006001.7, dated Jan. 31, 2013; 12 pages.

Australian Patent Examination Report for Patent Application No. 2008285169, dated Nov. 22, 2012; 4 pages.

Non-Final Office Action regarding U.S. Appl. No. 12/267,806, dated May 28, 2013; 15 pages.

Spindler, et al., "Poly-Pore, a microparticle delivery system: this material offers sustained release, protects sensitive materials and provides multifunctional benefits in personal care formulations," Household & Personal Products Industry, May 1, 2002.

Product specification of Reemay® Spunbonded Polyester Nonwovens, Style# 2214, found at http://filters.kavonfilter.com/item/filter-paper/reemay-spunbonded-polyester-nonwovens/item-1117? (1 page).

Second Examination Result received in Columbian Patent Application No. 11-95035, dated Oct. 18, 2013.

Extended European Search Report received in EP Patent Application 10735556.2, dated Mar. 6, 2014.

21 C.F.R. 350.3 (2008).

21 C.F.R. 350.10 (2008).

Chinese Second Office Action for Application No. 200980138546.0, dated Sep. 13, 2013; 15 pages.

Supplemental European Search Report for Patent Application No. 09824477.5-1303, dated Jun. 7, 2013; 4 pages.

First Office Action from Russian Patent Application No. 2011136300, dated Jan. 31, 2014; 3 pages.

Non-final Office action issued for U.S. Appl. No. 12/267,806 (dated Oct. 3, 2014).

Office action issued in Korean Patent Application No. 10-2011-7018003 (dated May 2016), 4 pages.

\* cited by examiner

ABSORBENT ARTICLES CONTAINING A MULTIFUNCTIONAL GEL

BACKGROUND OF THE DISCLOSURE

The present disclosure relates generally to absorbent articles for absorbing and holding bodily fluids and, more particularly, to absorbent articles that contain gels that exhibit adhesive and/or absorbent properties. Furthermore, it has been found that gels that possess both adhesive and absorbent qualities may be incorporated into absorbent articles. In one embodiment, the present disclosure relates to an absorbent article, such as a panty-liner, sanitary napkin, or an incontinence article, having the skin-adhesive and absorbent gel composition applied thereon for directly adhering the article to the skin of a user/wearer and for absorbing bodily fluids.

Absorbent personal care articles intended to absorb discharged bodily fluids are well known in the art. Such absorbent articles generally comprise a fibrous mass or other absorbent core which can absorb and hold body fluids. Similarly, it is well known that feminine care articles have been employed to absorb and hold liquids, such as urine and/or menses. Conventionally, absorbent articles include a fluid impermeable back sheet, a fluid permeable top sheet and an absorbent core positioned between the back sheet and the top sheet. Prior absorbent articles have also included various other features to improve fluid handling, such as intake layers, distribution layers, retention layers and the like. In these absorbent personal care articles, the top sheet is the body-facing side of the absorbent article and the back sheet is the garment-facing side of the absorbent article.

Generally, the absorbent articles are held in place during use by using the wearer's waist and elastic materials in the waist portion of the absorbent product in place during use, in the case of pant-like garments, such as diapers and training pants, or by attaching the absorbent article to the underwear or undergarment of a wearer, in the case of pads or panty-liners. Current methods of attaching the absorbent article to the underwear or undergarment of a wearer include utilizing an adhesive placed on the garment-facing side of the back sheet and, optionally or alternatively, utilizing flaps (wings) that extend from the longitudinal sides of the absorbent article which wrap around the crotch portion of the underwear or undergarment of the wearer.

It has also been suggested to use an adhesive to adhere the absorbent article to the skin of the wearer as described in U.S. application Ser. No. 12/267,806, the contents of which are incorporated herein for all relevant and consistent purposes.

A need exists for absorbent articles that include materials that are multifunctional and, specifically, materials that provide both absorption and adhesion to the wearer. Such absorbent articles would be characterized by decreased complexity. Further, an absorbent material that also functions as an adhesive would move as the body moves allowing for superior leak protection during periods of increased activity or movement by the wearer. Such a material would also reduce gapping between the material and the body of the wearer thus increasing fluid intercept and reducing the potential for fluid leak.

BRIEF DESCRIPTION OF THE DISCLOSURE

It has been found that skin-adhesive and absorbent gel compositions can be produced and included in absorbent articles for improved bonding of the substrates and articles directly to the skin of a user. Particularly, utilization of the skin-adhesive and absorbent gel compositions in absorbent articles reduces gapping between the material and the body of the wearer thus increasing fluid intercept and reducing the potential for fluid leak. Generally, the skin-adhesive and absorbent gel compositions of the present disclosure include hydrogels and/or aerogels that are skin-adhesive and absorbent. It has been found that the skin-adhesive and absorbent gel compositions allow the adhesive to maintain its bonding strength with the substrate and have improved bonding strength with the skin, yet remain gentle on the skin's surface. In one embodiment, the skin-adhesive and absorbent gel composition further includes at least one skin benefit agent for providing improved skin health to the user.

The skin-adhesive and absorbent gel composition may be applied to various substrates. Particularly, in one embodiment, the skin-adhesive and absorbent gel composition is applied to the body-facing side of a fluid-impermeable substrate of an absorbent article. Examples of absorbent articles include, for example, a panty-liner, sanitary napkin or incontinent article.

In one aspect of the present disclosure, an absorbent article comprises a fluid impermeable substrate having a body-facing surface and a garment-facing surface. The body-facing surface has a skin-adhesive and absorbent gel composition thereon for adhering the substrate directly to a wearer and for absorbing bodily fluids.

In another aspect of the present disclosure, an absorbent article comprises a fluid impermeable substrate, an absorbent core and a perforated liner. The fluid impermeable substrate has a body-facing surface and a garment-facing surface. The absorbent core is interposed between the substrate and perforated liner and comprises an absorbent gel composition.

Other objects and features will be in part apparent and in part pointed out hereinafter.

BRIEF DESCRIPTION OF THE DRAWINGS

Corresponding reference characters indicate corresponding parts throughout the drawings.

DEFINITIONS

Figure 1:
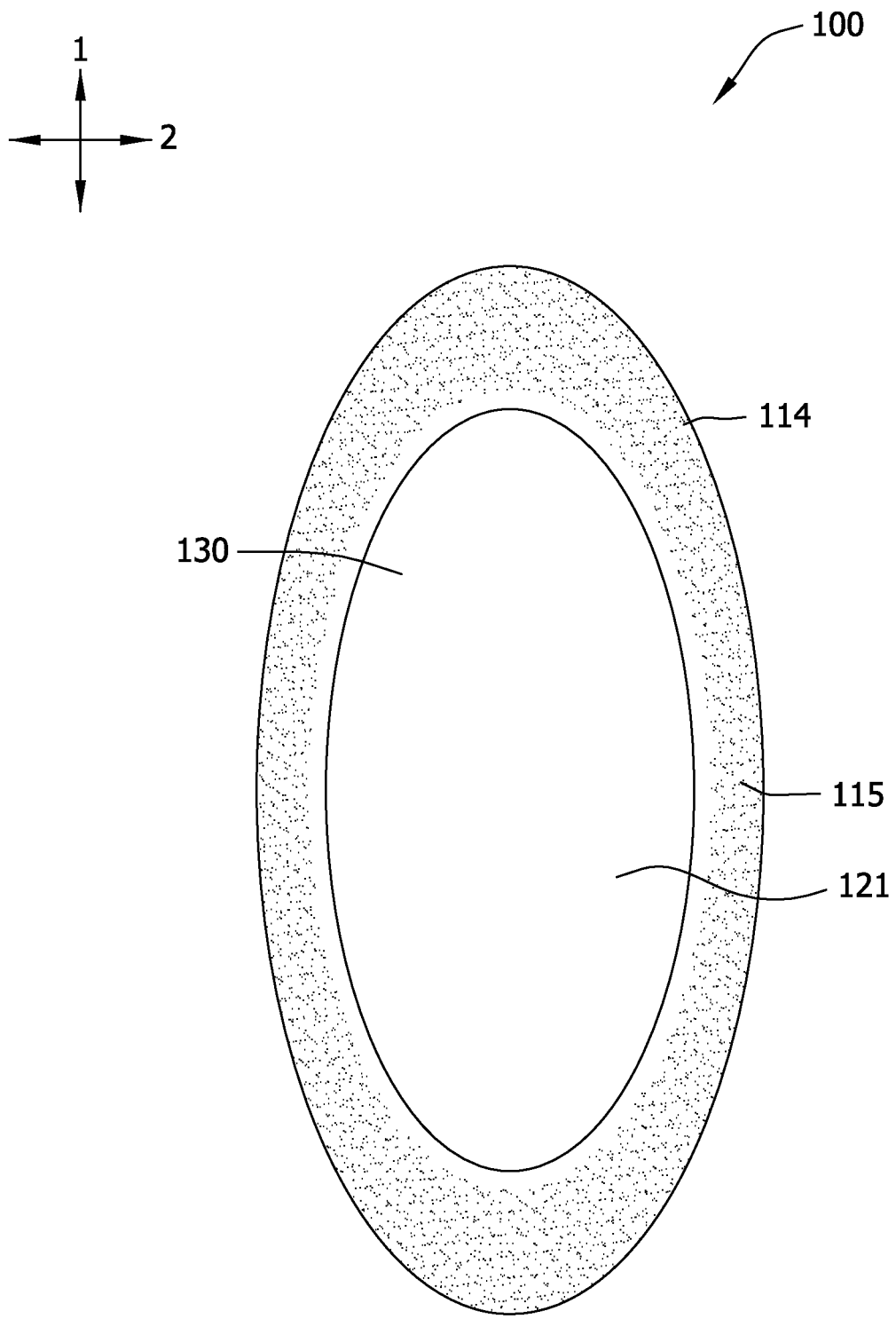
FIG. 1 shows a top view of an embodiment of an absorbent article of the present disclosure.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

When introducing elements of the present disclosure or the preferred embodiment(s) thereof, the articles "a", "an", "the" and "said" are intended to mean that there are one or more of the elements. The terms "comprising", "including"

and "having" are intended to be inclusive and mean that there may be additional elements other than the listed elements.

It should be understood that the term "absorbent product" or "absorbent article", as used herein, refers to any article used to control bodily fluids that are configured to absorb and retain bodily exudates, including urine, blood, menses, and other bodily discharges, such as sweat and vaginal secretions resulting from sexual activity and the like. In addition, the term is intended to include odor absorbing articles. Absorbent articles include diapers, tampons, incontinence articles, and the like.

As used herein, the term "polymer" generally includes, but is not limited to, homopolymers, copolymers, such as, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, "adhesion modifier" refers to an agent that allows the adhesive of the gel composition to maintain its bonding strength with the substrate and improve its bonding strength with skin, yet remain gentle on the skin's surface. Furthermore, the adhesion modifier behaves as a delivery vehicle or carrier to aid in the delivering of one or more skin benefit agents to the skin of the user. Typically, the adhesion modifier has a polymer-like or matrix network structure that may have numerous micropores or channels, which can hold the skin benefit agent as described below. Suitable adhesive modifiers may include, for example, POLY-PORES, POLY-TRAPS, and the like. Particularly suitable examples, described more fully below, include POLYTRAP 7603, which is an allyl methacrylate/glycol dimethacrylate crosspolymer; POLYTRAP 6603, which is a lauryl methacrylate/glycol dimethacrylate crosspolymer; POLY-PORE E200 and POLY-PORE L200, both of which are allyl methacrylate crosspolymers.

As used herein, "body-facing surface" means that surface of the absorbent article or any structure that is part of the absorbent article (for example, liner, absorbent core, gel composition) which is intended to be disposed toward or placed adjacent to the body or skin of the wearer during ordinary use. The "garment-facing surface" is on the opposite side of the absorbent article from the body-facing surface. The garment-facing surface is an outward surface of the fluid impermeable substrate and is intended to be disposed to face away from the wearer's body during ordinary use. The garment-facing surface is generally arranged to face toward or placed adjacent to the wearer's undergarments when the absorbent article is worn.

As used herein, the term "connected" is intended to mean directly connected and indirectly connected. By directly connected, it is intended that the connected elements are in contact with one another or affixed or adhered to one another. By indirectly connected, it is intended that one or more intervening or intermediate elements are between the two elements which are secured or "connected" together. The intervening elements may be affixed or adhered.

As used herein, the term "attached" is intended to mean directly attached and indirectly attached. By directly attached, it is intended that the attached elements are in contact with one another or affixed or adhered to one another. By indirectly attached, it is intended that one or more intervening or intermediate elements are between the two elements which are secured or "attached" together. The intervening elements may be affixed or adhered.

As used herein, the term "fluid impermeable substrate" is intended to mean any substrate known in the absorbent articles, health care products, and/or personal care product art that is generally capable of maintaining a dry garment-facing surface upon exposing the body-facing surface to water or other bodily fluids. Health care products include products such as masks, surgical gowns, gloves, and the like.

As used herein, the term "hydrogel" or "hydrogel composition" refers to a polymeric material that is capable of absorbing more than about 20% its weight in water while maintaining a distinct three-dimensional structure. Additionally, the term "hydrogel monomer" may refer to the polymerizing formulation or hydrogel precursor composition (including the hydrogel monomer) which is converted to a hydrogel when polymerization is triggered via conventional processes such as UV radiation (or UV curing), gamma rays, electron-beam, heat, chemical initiation, etc., as discussed elsewhere herein.

As used herein, the term "aerogel" refers to a low density material in which the liquid has been replaced by a gas. Aerogels include all aerogel forms including, for example, inorganic aerogels, organic aerogels (particularly carbon aerogels), and xerogels (gels formed when hydrogels are air dried as opposed to supercritically dried).

As used herein, the term "fibrous web" includes any web having a structure of individual threads (e.g., fibers or filaments), including woven webs, nonwoven webs, scrim, knitted webs, etc.

As used herein, the term "nonwoven web" refers to a web having a structure of individual threads (e.g., fibers or filaments) that are randomly interlaid, not in an identifiable manner as in a knitted fabric. Nonwoven webs include, for example, meltblown webs, spunbond webs, carded webs, wet-laid webs, airlaid webs, coform webs, hydraulically entangled webs, etc. The basis weight of the nonwoven web may generally vary, but is typically from about 5 $g/m^2$ to 200 $g/m^2$, in some embodiments from about 10 $g/m^2$ to about 150 $g/m^2$, and in some embodiments, from about 15 $g/m^2$ to about 100 $g/m^2$.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241, which is incorporated herein for all relevant and consistent purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous filaments. The filaments are formed by extruding a molten thermoplastic material from a plurality of fine, usually circular, capillaries of a spinnerette with the diameter of the extruded filaments then being rapidly reduced as by, for example, eductive drawing and/or other well-known spun-bonding mechanisms. The production of spunbond webs is described and illustrated, for example, in U.S. Pat. No. 4,340,563, U.S. Pat. No. 3,692,618, U.S. Pat. No. 3,802,817, U.S. Pat. No. 3,338,992, U.S. Pat. No. 3,341,394, U.S. Pat.

No. 3,502,763, U.S. Pat. No. 3,502,538, U.S. Pat. No. 3,542,615, and U.S. Pat. No. 5,382,400, which are incorporated herein for all relevant and consistent purposes. The filaments may, for example, have a length much greater than their diameter, such as a length to diameter ratio ("aspect ratio") greater than about 15,000:1, and in some cases, greater than about 50,000:1. The filaments may sometimes have diameters less than about 40 micrometers, and are often between about 5 to about 20 micrometers.

As used herein "carded webs" refers to nonwoven webs formed by carding processes as are known to those skilled in the art and further described, for example, in U.S. Pat. No. 4,488,928, which is incorporated herein for all relevant and consistent purposes. Briefly, carding processes involve starting with staple fibers in a bulky batt that is combed or otherwise treated to provide a generally uniform basis weight. A carded web may then be bonded by conventional means as known in the art such as, for example, through air bonding, ultrasonic bonding and thermal point bonding.

As used herein, an "airlaid" web is a fibrous web structure formed primarily by a process involving deposition of loose, air-entrained fibers onto a porous or foraminous forming surface. Generally, the web includes cellulosic fibers such as those from fluff pulp that have been separated from a mat of fibers, such as by a hammermilling process, and then entrained in a moving stream of air and deposited or collected on the forming screen or other foraminous forming surface, usually with the assistance of a vacuum supply, in order to form a dry-laid fiber web. There may also be other fibers such as thermoplastic staple fibers or binder fibers present, and typically following collection of the fibers on the forming surface the web is densified and/or bonded by such methods as thermal bonding or adhesive bonding. In addition, super absorbent materials in particulate or fiber form may be included in airlaid webs where desired. Equipment for producing air-laid webs includes the Rando-Weber air-former machine available from Rando Corporation of New York and the Dan-Web rotary screen air-former machine available from Dan-Web Forming of Risskov, Denmark.

DETAILED DESCRIPTION OF THE DISCLOSURE

Figure 2:
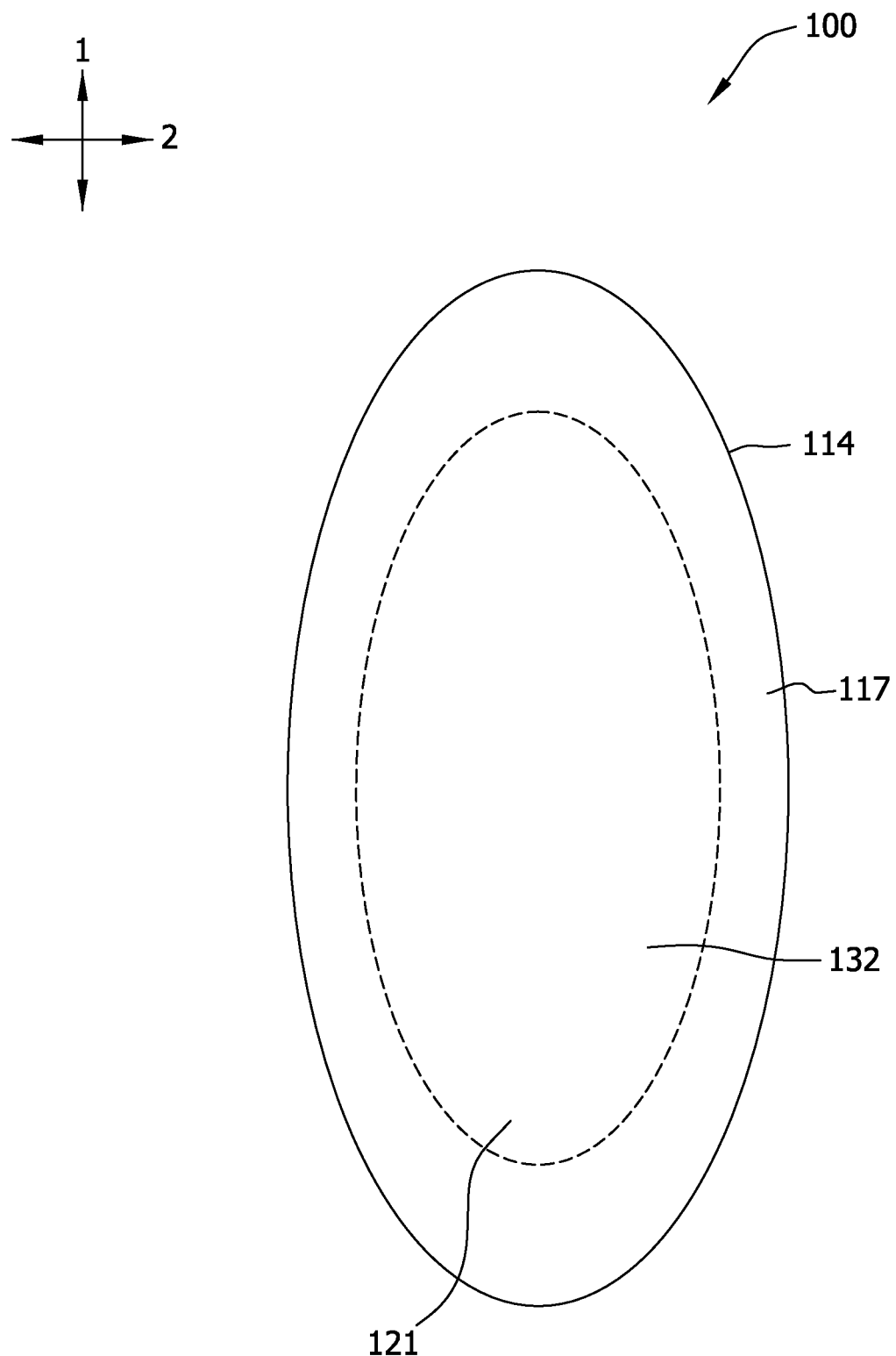
FIG. 2 shows a bottom view of the absorbent article shown in FIG. 1.

Referring now to FIG. 1, an absorbent article constructed generally in accordance with the principles of the present disclosure is designated as 100. As illustrated in FIGS. 1-2, the absorbent article 100 has a longitudinal direction 1 and a lateral direction 2. One component of the absorbent article 100 is a substrate 114. This substrate 114 has a first side 115, as shown in FIG. 1, and a second side 117, as shown in FIG. 2. The substrate 114 serves to provide the overall contour or silhouette of the absorbent article 100. In addition, the substrate 114 also provides a surface for attachment or adhesion of the absorbent article 100 to the body of a wearer.

The first side 115 of the substrate 114 is the body-facing side of the substrate and the second side 117 of the substrate is the garment-facing side. The first side 115 of the substrate 114 is generally designed or adapted for contact with the wearer's skin.

The absorbent article 100 has a skin-adhesive and absorbent gel composition 121 attached to the first side 115 of the substrate 114. The gel composition 121 has a first side 130 that is the body-facing side of the composition and a second side 132 that is the garment-facing side of the gel.

Generally, the substrate 114 is sized and shaped such that the first side 115 of the substrate only contacts or adheres to the skin surrounding and proximate to the vulva area and possibly the pubic and perinea regions of the wearer. The skin-adhesive and absorbent gel composition 121 is sized and shaped so that generally the first side 130 of the gel composition contacts the vulva region of the wearer. The first side 130 of the gel composition 121 is what holds the absorbent article in place on the body of a wearer.

The absorbent article 100 of the present disclosure is designed to adhere to the body of a wearer in the area of the body of the wearer which may need bodily fluids absorbed. In one particular use of the absorbent article, the absorbent article is attached to the body of a female wearer to or around the vulva region of the body. By "to or around the vulva region", it is meant adjacent regions of the body of a female including the vulva, pubic region and the perinea region. When applied to or around the vulva region of the female body, the absorbent article may be used as a panty-liner, sanitary napkin or incontinence article. In addition, the absorbent article may be worn as an underwear substitute since the absorbent article of the present disclosure does not need underwear to hold the absorbent article in place. As an underwear substitute, the absorbent article provides protection to the vulva area by creating a barrier between the outer clothing and the vulva of a wearer. When worn as an underwear substitute, the absorbent article serves to protect the outer clothing of the wearer from bodily discharges from the vulva region of the wearer's body. In addition, when the absorbent article is worn as an underwear substitute, the absorbent article also serves to protect the sensitive skin and body features of the vulva region from roughness of the outer clothing, thereby preventing or alleviating irritation to the sensitive skin and body features of the vulva region. While described herein as a female personal article such as a panty-liner or sanitary napkin, it should be recognized by one skilled in the art that the absorbent article can be any absorbent article in the personal care art, and further, the user need not be a female.

The Substrate

Figure 5:
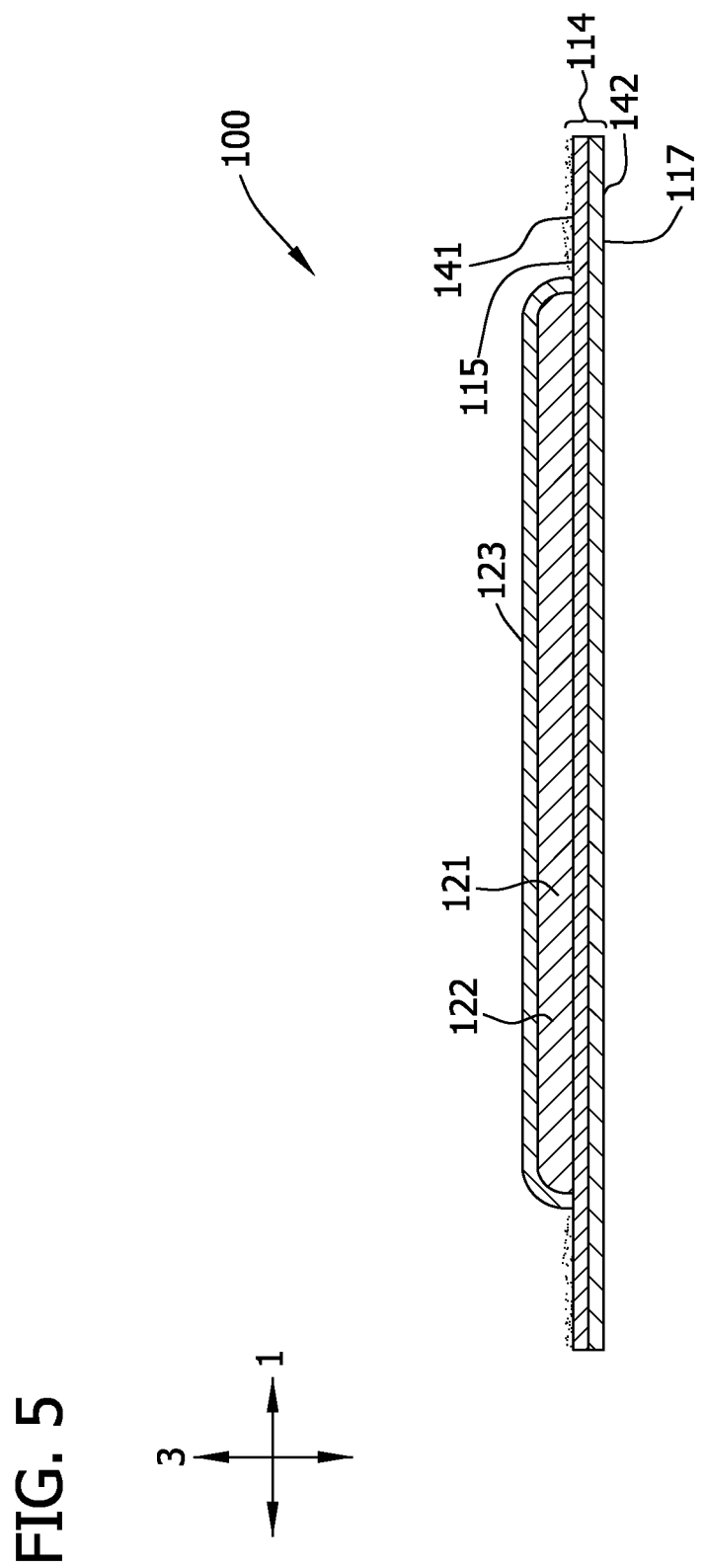
FIG. 5 shows a cross-section of a fourth embodiment of an absorbent article of the present disclosure.

The substrate 114 of the absorbent article 100 may be prepared from a variety of materials. The substrate may include a layer constructed of any material which will function to be operatively fluid impermeable. The substrate 114 may, for example, include a polymeric film, a woven fabric, a nonwoven fabric or the like, as well as combinations or composites thereof. For example, the substrate 114 may include a polymer film laminated to a woven or nonwoven fabric. A laminate substrate 114 structure is shown in FIG. 5, having an upper layer 141 and a lower layer 142, wherein the upper layer 141 is the body-facing side of the substrate 114 and the lower layer 142 is the garment-facing side of the substrate. In a particular embodiment, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored.

Suitably, the substrate 114 can operatively permit a sufficient passage of air and moisture vapor out of the absorbent article 100, particularly out of an skin-adhesive and absorbent gel composition 121 while blocking the passage of bodily fluids and odors often associated with bodily fluids. An example of a suitable substrate material can include a breathable, microporous film, such as those described in, for example, U.S. Pat. No. 6,045,900, which is incorporated herein by reference for all relevant and consistent purposes. Other substrate materials which are extensible may be used in the present disclosure, including, for example foams. One example of a suitable foam is a polyurethane foam with a negative Poissons ratio. Examples of extensible backsheet materials are described in U.S. Pat. No. 5,611,790, which is incorporated herein by reference for all relevant and consistent purposes. Other materials that are inherently breathable, such as polyurethanes, may be used to form the substrate 114.

In one particular embodiment of the present disclosure, the substrate 114 may be a laminate of a woven or nonwoven fabric with a silicone polymer. The second side 117 of the substrate will be woven or nonwoven fabric and the first side 115 of the substrate will be silicone polymer. One commercially available laminate is an OLEEVA FABRIC available from Bio Med Sciences, Inc. (Allentown, Pa.). The OLEEVA FABRIC is a silicone sheeting having adhesive properties laminated to a fabric backing. The silicone sheeting will form the body-facing first side 115 of the substrate material. Relating this particular structure to the Figures, in FIG. 5, the silicone polymer is the upper layer 141 of the substrate 114 and the nonwoven or woven layer is the lower layer 142 of the substrate. In one embodiment, the polymer film is composed of polyethylene, polypropylene, polyester, silicone or the like, as well as combinations thereof. Additionally, the polymer film may be micro-embossed, have a printed design, have a printed message to the consumer, and/or may be at least partially colored.

Bicomponent films or other multi-component films can also be used as the substrate 114 material. In addition, woven and/or nonwoven fabrics which have been treated to render them operatively liquid-impermeable may also be used as an effective substrate 114 material. Another suitable substrate material can include foams. Examples of foam include a closed-cell polyolefin foam, a foam with a negative Poissons ratio and other similar foams. Other suitable polymeric materials include a polyurethane polymer material, a silicone polymer or other similar materials.

In another embodiment of the present disclosure, the substrate 114 may be prepared from an interpenetrating polymer network or two or more polymers. Generally, one of the polymers of the interpenetrating polymer network may be a silicone gel. Examples of interpenetrating polymer networks are described in U.S. Pat. No. 5,759,560, which is incorporated herein by reference for all relevant and consistent purposes.

The substrate material should be selected such that the overall properties of the substrate allow the substrate material to move with the skin of the wearer during normal use and normal movements by the wearer during use. By "normal movement by the wearer" it is meant any movement that normally occurs during use of the absorbent article, including walking, running, sitting, standing, kneeling, riding a bicycle, exercising, playing sports, getting into and out of an automobile, and other similar movements made by wearers when wearing an absorbent article. The substrate 114 should not be too rigid, such that the substrate detaches from the skin of the wearer during use and the substrate should not be so flexible that the substrate tends to twist and bunch during use. The substrate 114 should have sufficient flexibility to conform to the skin of the wearer and become similar to a second skin of the wearer. The substrate 114 should also have the ability to remain attached to the body of the wearer under moist or wet conditions.

Generally, the substrate material should have sufficient thickness to allow the substrate 114 to mold to the body of the wearer, but not too thick that the substrate 114 becomes uncomfortable for the wearer to wear. In addition, the substrate 114 should not be so thin that it ineffectively forms a seal with the skin of the wearer when applied to the wearer, or becomes detached from the skin of the wearer during use and normal movement of the wearer during use or that it does not adequately conform to the shape and skin of the wearer at the point of attachment to the wearer. Depending on the material used for the substrate, the typical thickness of the substrate 114 is between 0.03 mm and about 5.0 mm and, more particularly between 0.1 mm and 3.0 mm. In one particular embodiment, the thickness of the substrate is between 0.25 mm and about 3.0 mm. Again, the actual thickness used is dependent of several factors including rigidity of the material, the flexibility of the material and the ability of the material to assume the shape of the skin of the wearer at the location of use.

The second side 117 of the substrate 114 may form a portion of the garment-facing side of the absorbent article 100 when worn by a wearer. The substrate material should be selected such that the second side 117 of the substrate 114 will freely move against the undergarment or clothing of a wearer. One way to achieve this result is to construct the second side 117 of the substrate 114 to have a fairly low coefficient of friction. This will allow the second side 117 of the substrate 114 to freely move against the undergarment or other clothing worn by the wearer. If the second side 117 of the substrate 114, does not freely move against the undergarment or other clothing worn by the wearer, the absorbent article may catch on the undergarment or clothing, which may result in the absorbent article being prematurely and undesirably removed from the wearer or may cause the absorbent article to be shifted from its desired placement against the body of a wearer.

In order to achieve the desired coefficient of friction on the second side 117 of the substrate 114, the materials used to prepare the substrate could be selected such that the second side of the substrate material will inherently have the desired coefficient of friction. Alternatively, the second side 117 of the substrate 114 may be treated with a coating composition, such a polytetrafluoroethylene-containing coating, a silicone-containing coating or other similar coating having low coefficient of friction properties. Alternatively, the substrate 114 could be made from a laminate of two or more materials such that the first side 115 of the substrate 114 is prepared from a material which meets the needed properties of the first side, while the material selected for the second side 117 of the substrate meets the desired coefficient of friction such that the second side will move freely against the undergarment or garment being worn by a wearer.

Figure 4:
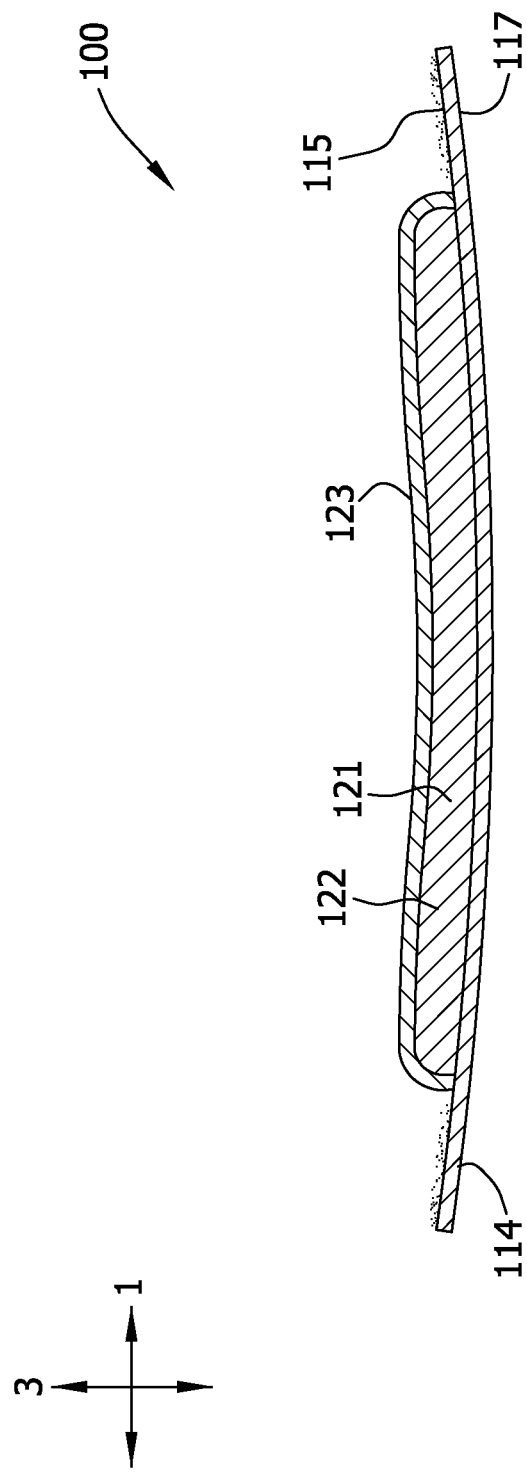
FIG. 4 shows a cross-section of a third embodiment of an absorbent article of the present disclosure.

The substrate 114 of the absorbent article 100 may be flat or may have a three-dimensional shape. As is shown in FIG. 4, which is a cross-sectional side view of an absorbent article of one embodiment of the present disclosure, the substrate 114 has a three-dimensional concave shape. Alternatively, as is shown in cross-sectional side views of FIG. 5, the substrate 114 may have a generally flat shape. By providing the absorbent article 100 with a three-dimensional concave shape, as is shown in FIG. 4, placement of the article may be easier for the wearer. Generally, the three-dimensional shape could be such that it closely matches the overall general curvature of the vulva region and optionally the pubic and perinea regions of most women, when the absorbent article is used as a panty-liner, sanitary napkin or a feminine incontinence article. To form the substrate 114 with a three-dimensional shape, the substrate may be molded in any manner known to those skilled in the art, for example heat molding. The manner in which the three-dimensional shape is imparted to the substrate 114 is not critical to the present disclosure.

When the substrate 114 is a generally flat shape, for example as shown in FIG. 5, meaning that the substrate does not generally have a third dimension other than thickness, the substrate should be made to be flexible enough that the substrate can conform to the body of the wearer at the point of attachment. In addition to being flat, the overall shape of the substrate 114 may be contoured. In one embodiment (not shown), the contour shape may be such that the narrowest point of the contour is in the crotch area of the substrate 114 nearest the vulva region. The contour shape is one of many possible shapes, in which the substrate 114 and absorbent article may be prepared. Other shapes may be used, without departing from the scope of the present disclosure. Generally, the shape selected should be such that the substrate 114 and absorbent article 100 are comfortable for the wearer to wear, while providing leakage protection to the wearer. It is noted that a contour shape may also be used in conjunction with a three-dimensional substrate.

The substrate may be any desired color or may be translucent. In addition, the substrate may have a matte finish, satin finish or a smooth finish. The particular finish color or translucency is a matter of choice for the manufacturer of the absorbent article of the present disclosure. However, providing a substrate 114 which is translucent may assist the wearer in placing the absorbent article 100 prior to use, since the wearer may be able to see where the article is placed compared to the genitalia of the wearer.

Skin-Adhesive and Absorbent Gel Compositions

Figure 3:
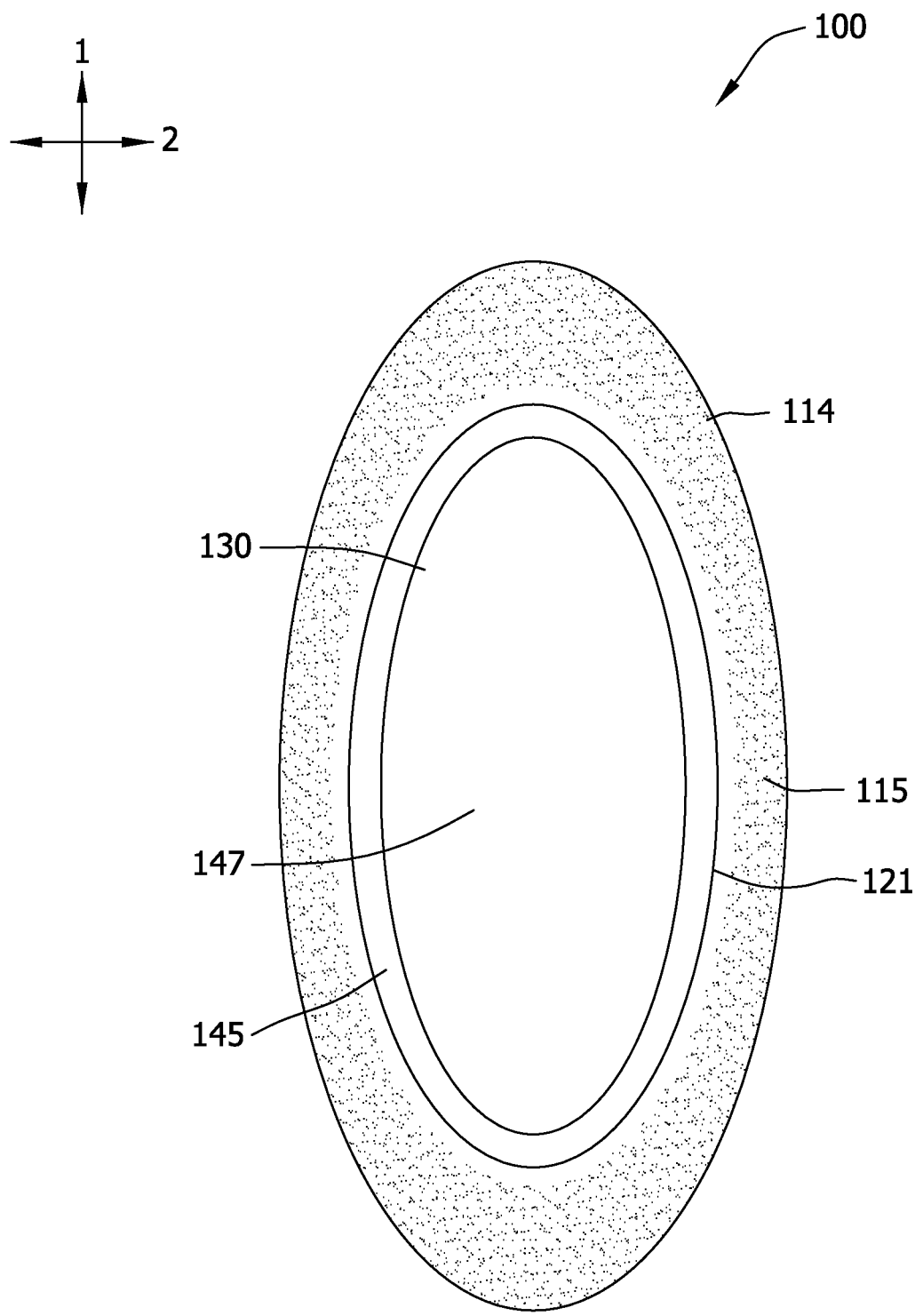
FIG. 3 shows a top view of a second embodiment of an absorbent article of the present disclosure.

The skin-adhesive and absorbent gel composition 121 is designed to absorb body exudates, including menstrual fluid, blood, urine, and other bodily fluids, such as sweat and vaginal discharges. The gel composition 121 has a longitudinal direction 1 and a lateral direction 2 and is shown in FIGS. 1-3, and a thickness in the z-direction 3, as is shown in FIGS. 4 and 5. Generally, the gel composition 121 will be positioned adjacent to the first side 115 of the substrate 114, as can be clearly seen in FIGS. 1-4. By "adjacent to the substrate", it is meant that the gel composition 121 is directly in contact with the first side 115 of the substrate 114 or may be separated by one or two additional layers or a construction or pressure sensitive adhesive.

In addition to absorbing bodily fluids, the gel composition 121 contacts the skin and hair, if present, in the vulva region and possibly the pubic region and/or the perinea region of the wearer's body, thereby supporting and holding the absorbent article 100 against the body of the wearer during use. The gel composition 121 should not be an irritant to human skin or be adhesive to the point where it causes pain to the user/wearer when the absorbent article is removed from the skin. The gel composition 121 should also not leave a substantial amount of residue on the surface of the skin of the wearer when absorbent article is removed by the wearer after use.

The gel composition 121 should form a sufficiently strong bond with the substrate 114 such as to prevent premature peeling or delaminating of the substrate or absorbent article; however, the gel composition needs to remain gently attached to the skin's surface so as to be easily and comfortably removed and/or reapplied. Accordingly, the gel composition 121 should provide a greater peel strength relating to the attachment between the gel composition and the substrate than the peel strength relating to the attachment between the gel composition and the surface of a user's skin. In one embodiment, the gel composition 121 provides a peel strength of gel composition to substrate of greater than about 800 grams per inch and, in other embodiments, from about 800 grams per inch to about 1500 grams per inch or from about 900 grams per inch to about 1000 grams per inch.

As the gel composition 121 is applied to the skin to keep the absorbent article 100 in position during use, the gel composition should possess a high peel strength of composition to skin to hold the absorbent article in place while remaining gentle on the skin's surface. In one embodiment, the gel composition has a peel strength of composition to skin of from about 5 grams per inch to about 100 grams per inch and in another embodiment from about 20 grams per inch to about 100 grams per inch. In other embodiments, the gel composition 121 has a peel strength of gel composition to skin of less than about 50 grams per inch, less than about 25 grams per inch, less than about 20 grams per inch or even less than about 5 grams per inch. In yet other embodiments, the gel composition has a peel strength of composition to skin of from about 75 grams per inch to about 500 grams per inch or even from about 100 grams per inch to about 200 grams per inch.

To measure peel strength of the skin-adhesive compositions, a method similar to STM 5599 may be used. STM 5599 is fully described in U.S. application Ser. No. 12/267,806, which is incorporated herein for all relevant and consistent purposes.

As shown in FIG. 1, the skin-adhesive and absorbent gel composition 121 can overlie a portion of the first side 115 of the substrate 114, however, the gel composition can overlie the entire first side of the substrate 114 without departing from the scope of the present disclosure. Generally, the gel composition 121 will be present on at least the central portion of the first side 115 of the substrate 114 near the center of the absorbent article 100. The gel composition 121 may also be placed in a pattern of the first side 115 of the absorbent article. The gel composition 121 may be applied to the first side 115 of the substrate 114 using any known process including inkjet printing, screen printing or extruding the skin-adhesive and absorbent composition from one or more nozzles, slot coating and the like.

The skin-adhesive and absorbent gel composition 121 may be positioned on the first side 115 of the substrate 114 in an open pattern or a closed pattern. By "open pattern" is meant that the composition has an intermittent or discontinuous pattern. For example, there may be breaks in the skin-adhesive and absorbent gel composition at certain portions of the first side 115 of the substrate 114. In one embodiment of an "open" pattern of the skin-adhesive and gel composition, individual beads of composition are applied in a discontinuous fashion. In a "closed pattern" the gel composition 121 is continuous. In the present disclosure, the closed pattern can be advantageous since the skin-adhesive and absorbent composition 121 may form a seal with the skin of the wearer which will assist in preventing leaks. Further, a closed pattern helps increase the surface area of the gel composition 121 that is available to absorb excreted bodily fluids.

In one embodiment of the present disclosure, the skin-adhesive and absorbent gel composition 121 is placed on the entire first side 115 of the substrate 114 (not shown). In another alternative embodiment of the present disclosure and as shown in FIGS. 1-5, the gel composition 121 is placed along the central portion of the first side 115 near the center of the substrate 114.

In one embodiment, the weight of skin-adhesive and absorbent gel composition 121 of the absorbent article 100 is from about 1 g/m$^2$ to about 450 g/m$^2$. In another embodiment, the weight of skin-adhesive and absorbent gel composition 121 of the absorbent article is from about 50 g/m² to about 150 g/m².

In some embodiments, the gel composition is capable of absorbing up to about 20%, up to about 50%, up to about 100%, up to about 250% or even up to about 1000% of its weight in water and, suitably, bodily fluids.

The water content of the gel composition may be determined as follows:

$$\% \text{ water content} = 100 \times (W_w - W_d)/W_w$$

wherein $W_w$ is the weight of the wet gel composition and $W_d$ is the weight of dry composition.

Generally, the gel composition 121 is applied in a manner which is symmetrical about the longitudinal axis which bisects the absorbent article 100 and divides the absorbent article 100 into substantially equal portions. This symmetrical pattern provides the wearer a balanced feel when wearing the absorbent article 100. The symmetrical pattern also reduces the perception of any associated discomfort when the absorbent article 100 is removed from the body.

The thickness in the z-direction of the gel composition influences the absorptive capacity of the composition with thicker compositions being generally capable of absorbing more fluid than thinner compositions.

In one embodiment, the skin-adhesive and absorbent gel composition 121 of the absorbent article 100 is defined by a central portion 147 and a peripheral portion 145 (FIG. 3). The peripheral portion 145 which, in some embodiments, surrounds and is proximate to the vulva area and possibly the pubic and perinea regions of the wearer may be more adhesive to the skin of the wearer than the central portion 147. The central portion 147 which, in some embodiments, is more likely to contact bodily fluids including, for example, menses and urine, may be more absorbent than the peripheral portion 145. The central portion 147 may also contain apertures, perforations and/or pores for directing fluid inward into the gel composition 121. The peripheral portion 145 may extend to the edge of the substrate 114 without departing from the scope of the present disclosure.

The gel composition 121 may be a single layer or may be multiple gel layers (not shown) which aid in skin-adhesion and/or capturing and holding of bodily fluid. In one embodiment, the gel composition has a substrate-adjacent layer and a body-facing layer. The substrate-adjacent layer may be more hydrophilic than the body-facing layer to help draw fluids away from the skin of the wearer and to the portions of the gel composition 121 furthest from the skin of the wearer.

The surface of the skin-adhesive and absorbent gel composition 121 may be modified to produce different nanostructures and/or microstructures at the surface of the composition. The surface may be manipulated to change the thermodynamic, chemical and/or biological interaction of the gel composition 121 with the skin. For example, the surface may be modified to reduce the adhesive pull-off force with the skin or be modified to act as a basement membrane of scaffold for skin health and tissue regeneration. An example of a modification of the surface of a polymer adhesive is described in Mahdavi et al., "A Biodegradable and Biocompatible Gecko-inspired Tissue Adhesive," PNAS, vol. 105: 7, pp. 2307-2312, the entire contents of which are incorporated herein for all relevant and consistent purposes.

In one embodiment, the skin-adhesive and absorbent gel composition 121 is a coating that covers the individual threads of a nonwoven substrate 114. The gel composition coating may be applied by coating the target portions of the nonwoven substrate with a gel precursor composition and initiating polymerization as more fully described below. The thickness of the coating may be varied throughout the thickness of the nonwoven substrate. For example, the coating of the gel composition 121 upon the threads of the nonwoven substrate may be thicker near the portion of the garment-facing surface of the absorbent article 100 with the thickness generally decreasing toward the body-facing surface of the article to help draw fluid away from the skin of the wearer.

The absorbent article 100 may contain fluid-modifying components in the substrate 114 or the gel composition 121. Such fluid-modifying components include anti-fouling agents that prevent attachment of the absorbed bodily fluids to the fibrous network (more fully described below) within the absorbent article. Such anti-fouling agents prevent the pores of the article 100 from becoming plugged and allow the article to be worn for a longer period of time without replacement. Another example of a fluid-modifying component is a coagulant which causes the absorbed fluid to coagulate and/or thicken when contacted with the coagulant. Typically the coagulant is located near the garment-facing surface of the article rather than near the body-facing surface of the article in order to "lock" absorbed fluids away from the skin and give the wearer a sensation of dryness. Coagulants include, for example, psyllium husk, zeolites, chitosan and polysaccharides.

The absorbent article 100 may contain a superabsorbent material which increases the ability of the gel composition 121 to absorb a large amount of fluid in relation to its own weight. Generally stated, the superabsorbent material can be a water-swellable, generally water-insoluble, polymeric absorbent material, which is capable of absorbing at least about 15, suitably about 30, and possibly about 60 times or more its weight in physiological saline (e.g., saline with 0.9 wt % NaCl).

The absorbent article 100, including the substrate 114 and gel composition 121, should be sufficiently malleable and/or elastic such that the article conforms to the contours of the body as the wearer moves during a daily routine. The gel composition 121 should be able to conform to differing vulva dimensions and to the presence of public hair such that the gel composition provides a continuous fluid-impermeable seal. The measure of conformability may be determined and measured as described in U.S. Patent Publication No. 2004/0116883, the contents of which are incorporated herein be reference for all relevant and consistent purposes. In one embodiment, the gel composition 121 has a gap-protrusion area of at least about 20 mm² and, in another embodiment, at least about 40 mm².

Utilization of a Perforated Liner

Referring now to FIGS. 4 and 5, in one embodiment, the absorbent article 100 includes an absorbent core 122 and a perforated liner 123. The perforated liner 123 may be placed between the absorbent core 122 and the body of the wearer such that the absorbent core 122 is between the perforated liner 123 and the substrate 114. In this arrangement, fluid passes through the perforations of the perforated liner 123 and is absorbed in the absorbent core 122. Because the liner 123 separates the absorbed fluid from the skin of the wearer, the absorbent article provides a sensation of dryness to the wearer.

The absorbent core 122 may include any material that generally absorbs bodily fluids and, in one embodiment, includes an absorbent gel composition. In one particular embodiment, the absorbent core 122 includes an absorbent hydrogel composition and, in another embodiment, comprises an aerogel composition. Hydrogel and aerogel compositions are more fully described below.

The perforated liner 123 may be perforated according to any methods known in the art including, for example, a series of slits or a series of holes sized and adapted to allow bodily fluids (for example, menses) to pass. The perforated liner 123 may be constructed of many materials and, for example, may be a polymeric film, a woven fabric, a nonwoven fabric or the like, as well as combinations or composites thereof. Optionally, the perforated liner 123 may be formed from one or more materials. The perforated liner 123 should be able to manage different body excretions depending on the type of product. In feminine care products, often the perforated liner 123 must be able to handle menses and urine. In addition, the perforated liner 123 may be comfortable, soft and friendly to the wearer's skin. In the present disclosure, the perforated liner 123 may include a layer constructed of any operative material, and may be a composite material. For example, the perforated liner 123 may include a woven fabric, a nonwoven fabric, a polymer film, a film-nonwoven fabric laminate or the like, as well as combinations thereof. Examples of a nonwoven fabric useable in the perforated liner include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the perforated liner 123 can include bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers or biocomponent or biconstituent fibers thereof, polyesters in general including aliphatic esters such as polylactic acid, nylon or any other heat-bondable materials. Some minor amount of non-thermoplastic fibers (less than 50% by weight) such as rayon or lyocell may be blended with the heat-bondabale fibers.

In one embodiment, the perforated liner 123 is a hydrophobic material or is a material that is less hydrophilic than the material of the absorbent core 122. In another embodiment, the perforated liner 123 is a hydrophobic silicone gel.

Other examples of suitable materials for the perforated liner 123 are composite materials of a polymer and a nonwoven fabric material. The composite materials are typically in the form of integral sheets generally formed by the extrusion of a polymer onto a nonwoven web, such as a spunbond material. In a particular arrangement, the perforated liner 123 may be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent core 122). The selected arrangement of liquid permeability is desirably present at least on an operative portion of the perforated liner 123 that is appointed for placement on the body-side of the article. The perforated liner 123 can provide comfort and conformability, and can function to direct bodily exudates away from the body and toward the absorbent core 122. The perforated liner 123 can be configured to retain little or no liquid in its structure, and can be configured to provide a relatively comfortable and non-irritating surface next to the skin of a wearer. In the present disclosure, the perforated liner 123 positioned over the absorbent core 122 may have a surface which is embossed, printed or otherwise imparted with a pattern.

In one embodiment, the perforated liner 123 is sized and shaped to cover the vulva region of a wearer. This allows a portion of the absorbent core 122 to not be covered by the liner 123. The portion of the core 122 not covered by the liner 123 may be utilized to adhere the absorbent article to the wearer.

Additional layers or substrates, including for example, a liquid acquisition and distribution layer (not shown), also referred to as a surge or transfer layer, and an optional tissue layer may also be incorporated into the absorbent product 100, for example, between the perforated liner 123 and the absorbent core 122. The distribution layer may be shorter than the absorbent core or have the same length as the absorbent core 122. The distribution layer serves to temporarily hold an insulting fluid to allow the absorbent core 122 sufficient time to absorb the fluid, especially when a super-absorbent material is present.

Skin-Adhesive and Absorbent Hydrogel Compositions

The present disclosure makes provision for gel compositions for both absorbing bodily fluids and for bonding a substrate, such as an absorbent article, to skin. These multi-functional gel compositions allow the article to better move with the body allowing for superior leak protection and result in a reduction in gapping between the material and the body of the wearer thus increasing fluid intercept and reducing the potential for fluid leak.

The gel compositions described herein may be suitable for use as the skin-adhesive and absorbent gel composition 121 illustrated in FIGS. 1-3 and as the absorbent material of the absorbent core 122 illustrated in FIGS. 4 and 5. While the gel composition of the absorbent core 122 need not be skin-adhesive as skin-adhesion may be provided by the liner 123, the gel composition of the absorbent core may be adhesive and absorbent without departing from the scope of the present disclosure. Descriptions herein relating to "skin-adhesive and absorbent gel compositions" are also applicable to "absorbent gel compositions" suitable for the absorbent core 122 of the absorbent articles 100 illustrated in FIGS. 4 and 5.

The skin-adhesive and absorbent gel compositions are generally compatible with substrates and absorbent articles. Particularly, while described in terms of using the skin-adhesive and absorbent gel composition with an absorbent article, it should be recognized that the skin-adhesive and absorbent gel composition can be used with any of the substrates used for the components of the absorbent article, or any other substrate known in the personal care art.

In one embodiment, the skin-adhesive and absorbent gel composition is a hydrogel (synonymously "hydrogel composition"). The hydrogel may be a polymerization reaction product of a hydrogel precursor composition as described in U.S. patent application Ser. No. 11/709,996, which is incorporated herein for all relevant and consistent purposes.

The hydrogel composition may suitably be any color and, in one embodiment, may be a clear gel solution. Clear gel solutions contain an absence of precipitates or a limited amount of precipitates and are demonstrated when there is no residue or precipitates visible in the formulation with the naked or unaided eye.

In one embodiment, the hydrogel composition is formed from a precursor composition that includes a monomer, initiator, cross-linking agent and solvent. While any suitable monomer may be used, exemplary functional monomers include N-vinyl pyrrolidone (NVP), hydroxyethyl methacrylate (HEMA), methacrylic acid (MA) or its salt, styrene sulfonic acid (SSA) or its salt, potassium sulfopropyl acrylate (KPSA), dimethyl acrylamide (DMA), dimethyl amino ethyl methacrylate (DMAEMA) or its quaternary salt derivative, acrylamido methyl propane sulfonic acid (AMPS) or its salt, and the combination of any of the above. Additionally, the acid and salt of an exemplary functional monomer may be included in the hydrogel. In one embodiment, the hydrogels are made from various classes of monomers including acrylates, vinyls, amides, esters, etc, of which can be electrically neutral, cationic or anionic. Monomers may also be combined to achieve desired adhesion and/or absorbent properties.

In one particular embodiment, acrylamido methyl propane sulfonic acid (AMPS), or its salt, is used as the hydrogel monomer, either alone or in combination with another comonomer. Generally, AMPS is highly hydrophilic, is easy to work with, and polymerizes relatively easily. Also, AMPS, as a monomer, has a relatively favorable safety profile. As such, AMPS or its salt may be suitable for large scale production of a hydrogel precursor composition.

In one embodiment, the hydrogel is a cationic acrylate hydrogel. A cationic acrylate hydrogel suitable for use will generally be somewhat clear in color, viscous, and tacky to the touch. The hydrogel tends to be sufficiently adhesive to a subject's skin, yet sufficiently cohesive to be easily removable from the subject's skin and separable from itself. Examples of specific desirable cationic acrylates are: acryloyloxyethyltrimethyl ammonium chloride which is readily available from CPS Chemical Co. (New Jersey) or Allied Colloid (U.K.); acryloyloxyethyltrimethyl ammonium methyl sulfate which is also available from CPS Chemical Co. or Allied Colloid; and, acrylamidopropyltrimethyl ammonium chloride, which is available from Evonik Degussa (Germany). A process for making hydrogels with these exemplary acrylates is described in detail below.

In one embodiment, the monomer is from about 10% to about 80% by weight of the composition and, in another embodiment, from about 40% to about 75% by weight of the composition and even from about 50% to about 75% by weight of the composition.

The hydrogel compositions may be formed by in-situ free radical polymerization of a water soluble monomer in the presence of water, desirably by ultra-violet curing with at least one initiator, multi-functional cross-linking agent(s), and a solvent. For example, an appropriate acrylate monomer, water, electrolyte (e.g. sodium sulfate), initiator or catalyst (e.g., 1-hydroxycyclohexylphenol ketone, etc.), multi-functional cross-linker (e.g., methylene-bis-acrylamide, etc.), and solvent (e.g., dimethyl sulfoxide) are combined, placed in a mold, and exposed to an appropriate amount of ultra-violet radiation.

The hydrogel monomer can also be combined with at least one co-monomer to form the hydrogel precursor composition. Examples of co-monomers which may be used include co-monomers soluble in water and, even more desirably, include anionic co-monomers. In one embodiment, the amount of co-monomer to be used may be in the range of about 5 to about 50% by weight, desirably about 10 to about 30% by weight, based on the amount of reactants used. Examples of suitable co-monomers include unsaturated organic carboxylic acids such as acrylic acid, methacrylic acid, maleic acid, itaconic acid, and citraconic acid and salts thereof, unsaturated organic sulfonic acids such as styrene sulfonic acid, methallyl sulfonic acid, 2-sulfoethyl acrylate, 2-sulfoethyl methacrylate, 3-sulfopropyl acrylate, 3-sulfopropyl methacrylate, acrylamido-methylpropane sulfonic acid and salts thereof, N,N-dimethylacrylamide, vinyl acetate, other radically polymerizable ionic monomers containing a carbon-carbon double bond, and non-N-vinyl lactam co-monomers useful with N-vinyl lactam monomeric units such as N-vinyl-2-pyrrolidone, N-vinyl-2-valerolactam, N-vinyl-2-caprolactam, and mixtures thereof. Among the ionic monomers enumerated above, particularly desirable selections are 3-sulfopropylacrylate or methacrylate, and salts thereof. Another desirable selection is 2-acrylamido-2-methyl propane sulfonic acid and salts thereof. Examples of cations involved in the formation of such salts include sodium, potassium, lithium, and ammonium ions. Ionic monomers may be used singly or in a mixture of two or more monomers.

Any suitable solvent may be used. The desirability of a specific solvent and/or the amount thereof may vary or depend in part on the other components and quantities thereof selected to make up the hydrogel precursor composition. The use of any solvent capable of dissolving the initiator up to an amount equal to the initiator's solubility limit is desired. In some embodiments, the solvent is an organic solvent such as, for example, dimethyl sulfoxide and glycerine. In other embodiments, water is the solvent used in the hydrogel precursor composition.

The solvent is adapted to dissolve the initiator (hydrophobic or hydrophilic) and is water soluble. The solvent may be adapted to dissolve hydrophobic additives such as lipids, anti-oxidants, drugs, and fragrances. Additionally, the solvent may be adapted to dissolve skin benefit agent(s) described below.

In one embodiment, the solvent is present in an amount up to about 20% by weight of the hydrogel precursor composition and, in another embodiment, from about 0.5% to about 5% by weight of the hydrogel precursor composition.

The hydrogel precursor composition may also include a solubilizer to enhance the polymerization of the monomer, crosslinker, and/or initiator, such as described in U.S. Pat. No. 7,045,559, which is incorporated herein for all relevant and consistent purposes. Any suitable solubilizer or combination of solubilizers is contemplated. The desirability of a specific solubilizer and/or the amount thereof which is included in hydrogel precursor composition may vary or depend in part on the other components and quantities thereof selected to make up the hydrogel precursor composition. Exemplary solubilizers include, for example, cyclodextrin, cyclodextrin derivatives, and hydrotropes. Specific exemplary cyclodextrin derivative solubilizers include, for example, hydroxypropyl β-cyclodextrin (HP-β-CD) (available from Cargill Dow, Minnetonka, Minn.), γ-cyclodextrin (γ-CD) (available from Wacker Biochem Corporation, Adrian, Mich.) and other polymerizable cyclodextrin derivatives such as methacryloyl cyclodextrin. In a particular embodiment, the solubilizer is dimethyl sulfoxide (DMSO). In another particular embodiment, the solubilizer is glycerin. In one embodiment, the solubilizer is present up to about 20% by weight of the hydrogel precursor composition and, in another embodiment, between about 0.5% to about 5% by weight of the hydrogel precursor composition.

The hydrogel composition may include an optional buffer system to help control the pH, prevent discoloration (for example, to prevent yellowing of the hydrogel), and/or prevent breakdown due to an extended presence of water (i.e., hydrolysis). The use of a buffer system with the hydrogel composition is desired to provide the hydrogel with a commercially suitable shelf-life (i.e., a shelf-life of over one year) without discoloration. Suitable buffers include, but are not limited to, conventional buffers such as sodium hydroxide, sodium potassium tartarate, and/or sodium phosphate monobasic, all of which are commercially readily available from Aldrich Chemical Co., Inc., Milwaukee, Wis. The pH of the hydrogel composition may be adjusted as desired. In one embodiment, the compositions includes sufficient buffer to maintain the pH of the hydrogel in a range of about 3 to about 8.5, and, in another embodiment, from about 5.5 to about 7. In one embodiment, a buffer is present in the hydrogel precursor composition in an amount up to about 10% by weight, and, in another embodiment, from about 0 to about 5% by weight of the hydrogel precursor composition.

As an alternative to the use of conventional buffers, an amount of the acidic form of the monomer used may be used in the hydrogel precursor composition to adjust the pH of the hydrogel composition. An amount of the acidic form of the monomer will be combined with the salt of the monomer so that an additional conventional buffer may not be needed. In this regard, pH is conventionally adjusted in hydrogels by utilizing a dual buffer system including a non-monomeric acidic salt such as an aluminum potassium sulfate and an additional buffer having a pH greater than 7 such as sodium hydroxide. For example, conventionally, aluminum potassium sulfate, or another non-monomeric acidic salt, is added to the hydrogel precursor composition in an amount to stabilize the resulting polymer, however, the amount utilized may result in an unacceptable drop in pH. Because of this drop in pH, sodium hydroxide, or another buffer having a pH greater than 7, is added to the hydrogel precursor composition to bring the pH up to a satisfactory level.

Additionally, an acidic salt may be used by itself, and not as part of a dual buffer system, to maintain the pH in the desired range. However, utilizing the salt of the monomer in conjunction with the acid (as a pH adjuster) eliminates potential problems such as buffer incompatibility with the monomer while still increasing shelf life and stability of the monomer solution.

Other additives may be added such as, for example, skin benefit agents as described below. These other additives may be included either before or after a curing step. The appropriateness of such additives is generally dependent upon the intended end use of the particular hydrogel. Any suitable additive or combination of additives such as those suggested above or below is contemplated. The specific additive and/or the amount thereof which is included may vary or depend in part on the other components and quantities thereof selected to make up the hydrogel.

The skin benefit agent may optionally not be present in the hydrogel but may act as a separate hypoallergenic layer in communication with the hydrogel in order to reduce skin irritation of the wearer.

Initiators may be used in the polymerization of the hydrogel precursor compositions described herein. Examples of initiators which may be used include IRGACURE 184 (1-hydroxycyclohexyl phenyl ketone), IRGACURE 2959 (4-(2-hydroxyethoxy)phenyl-(2-hydroxy-2-methylpropyl)ketone)), and DAROCUR 1173 (2-hydroxy-2-methyl-1-phenyl-propan-1-one), all commercially available from Ciba Specialty Chemicals. These ultraviolet UV initiators are non-yellowing. Additional examples of suitable initiators (which may be photo initiators or thermal initiators) may include benzoyl peroxide, azo-bis-isobutyronitrile, di-t-butyl peroxide, bromyl peroxide, cumyl peroxide, lauroyl peroxide, isopropyl percarbonate, methylethyl ketone peroxide, cyclohexane peroxide, tutylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), acetophenones (such as acetophenone, trichloroacetophenone, 2,2-diethoxyacetophenone, p-t-butyltrichloro-acetophenone, 2,2-dimethoxy-2-phenyl-acetophenone, and p-dimethylaminoacetophenone), thioxanthones (such as xanthone, thioxanthone, 2-chlorothioxanthone, and 2-isopropylthioxanthone), benzyl 2-ethyl anthraquinone, methylbenzoyl formate, 2-hydroxy-2-methyl-1-phenylpropane-1-one, 2-hydroxy-4'-isopropyl-2-methyl propiophenone, α-hydroxy ketone, tetramethyl thiuram monosulfide, allyl diazonium salt, and combinations of camphorquinone and ethyl 4-(N, N-dimethylamino)benzoate. Other suitable initiators may be found in, for example, Berner, et al., "Photo Initiators—An Overview", J. Radiation Curing (April 1979), pp. 29.

Although only one initiator is typically used in the hydrogel precursor composition, the composition may contain one or more second initiators. The one or more second initiators can be photo or chemical initiators.

In one embodiment, the amount of initiator is from about 0.01% to about 5% by weight of the hydrogel precursor composition and, in another embodiment, from about 0.05% to about 2% by weight of the hydrogel precursor composition and, in yet another embodiment, from about 0.1% to about 0.5% by weight of the hydrogel precursor composition. Where one or more second initiators are present, the amount of one or more second initiators in some embodiments is from about 0.01% to about 5%, from about 0.05% to about 2% or from about 0.1% to about 0.5% by weight of the hydrogel precursor composition. Where multiple initiators are present, it is preferred that the combined amount of the initiators be about 5% or less by weight of the hydrogel precursor composition and, in another embodiment, from about 0.02% to about 5% by weight of the hydrogel precursor composition.

UV curing parameters that achieve desired polymer properties are conventional and within the skill of the skilled artisan. A photo initiator tends to operate by absorbing select wavelengths of UV to produce radical initiating species to induce monomer polymerization. The wavelengths and curing area set the style of UV bulb used in the curing process. Inhibition of polymerization due to dissolved oxygen, monomer inhibitors, or other radical scavenging moieties may be overcome by changing the power, by pulsing, and/or by using initiator accelerators.

Each photo initiator is typically responsive to a specific or narrow wavelength range of UV light. In one embodiment of the present disclosure, two or more photo initiators are included in a hydrogel precursor composition. The addition of more than one initiator in a hydrogel precursor composition allows for a broader range of the energy or range of wavelengths emitted by a UV source to be utilized. The utilization of multiple initiators can further reduce solubility limit concerns and related compatibility concerns, as more efficient polymerization may be able to be achieved with two initiators present in a hydrogel precursor composition than with either of the initiators used alone at the same overall initiator concentration.

The synergistic effect of initiators has not been previously identified or exhibited in previous hydrogels which incorporated one photo initiator, if any initiator at all. It is further believed that the inclusion of initiators having different rates of initiation and/or the inclusion of initiators which begin initiation of polymerization of the monomer at different times relative to each other (such as that which may be experienced by multiple initiators (e.g., a thermally activated chemical initiator (TACI) and a photo initiator)) contributes to a higher yielding polymerization. That is, for example, where two photo initiators are included, one may have a lower UV wavelength trigger and may be more energetic (providing for a faster rate of initiation and reaction) than the other initiator which is triggered by a higher UV wavelength or range. The faster initiator may also die or be consumed faster than the other. It is contemplated that it may be advantageous to have polymerization occur at different rates and/or at a mixed rate which may not be obtainable with one initiator or with an initiator which is suitable for a particular hydrogel precursor composition. An example of initiators which are not triggered or activated simultaneously, includes utilization of a photo initiator and a TACI in the hydrogel precursor composition wherein the photo initiator is triggered by a UV source and reacts with the monomers in the precursor composition so as to generate heat to trigger the TACI.

While numerous combinations and variations of initiators are possible, it is believed that the combination of multiple initiators provides more favorable kinetics which affords a higher probability of more extensive polymerization of the monomer and/or other monomeric residues.

In one embodiment, a TACI is included in the hydrogel precursor composition to take advantage of the benefits of multiple initiator polymerization. As some heat is necessary to trigger a TACI, it is contemplated that a TACI will generally be included only where heat will be present in or produced in the hydrogel precursor composition in a sufficient amount to trigger the TACI. As radical polymerization reactions induced by photo initiators are known to be exothermic and thus to generate heat in response to UV exposure, TACI may be included in a hydrogel precursor composition where a photo initiator is also present so as to allow the TACI to take advantage of the heat generated by the radical polymerization reaction induced by a photo initiator. It is also contemplated that a TACI can be included where multiple photo initiators are present. The presence of multiple photo initiators provides for the potential benefits of multiple initiators discussed above yet also provides for the triggering of a TACI where the heat generated by one photo initiator may be insufficient to trigger or fully trigger the TACI (depending on the photo initiators and the TACI involved), whereby the TACI can further promote or complete the polymerization of the functional monomer and other monomeric residues in a hydrogel precursor composition. Multiple TACIs may also be used.

Cross-linking agents may be used to crosslink the hydrogels. Multi-functional cross-linking agents which may be used include, for example, methylene-bis-acrylamide and diethylene glycol diacrylate which are both commercially available from Polysciences, Inc., Warrington, Pa. Other cross-linking agents which may be used include poly(ethylene glycol)diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis(N-vinyl-2-pyrrolidone), trimethylolpropate trimethacrylate, glycerol trimethacrylate, polyethylene glycol dimethacrylate, and other multifunctional polyacrylate and polymethacrylate crosslinkers.

In one embodiment, the amount of cross-linking agent present in the hydrogel precursor composition is from about 0.01% to about 2% by weight of the hydrogel precursor composition and, in another embodiment, from about 0.05% to about 0.5% by weight of the hydrogel precursor composition.

Regardless of the technique utilized, crosslinking forms a hydrogel constituted by a three-dimensional network that is substantially water-insoluble. Upon absorbing water, the hydrogel swells, thereby increasing the area between cross-links to form pores. For example, at its highest water content, the hydrogel may possess pores having an average size of from about 1 nanometer to about 10 microns, in some embodiments from about 10 nanometers to about 1 micron, and in some embodiments, from about 50 nanometers to about 100 nanometers. Thus, when exposed to water, the hydrogel does not dissolve, but instead may absorb a certain amount of water. Thus, the hydrogel composition is capable of absorbing bodily fluids.

In some embodiments, at least one surfactant is included in the hydrogel precursor composition or added to the hydrogel. It is believed that the presence of a surfactant can increase the rate of absorbency of water and moisture of the hydrogel. Exemplary surfactants include, for example, alkyl polyglycosides; silicones modified to contain alkyl, polyglycol, and/or amino groups (e.g., ethyoxylated polydimethyl siloxanes); alkylphenol ethoxylate surfactant; and the like. Commercially available examples of suitable alkyl polyglycosides include Glucopon 220, 225, 425, 600 and 625, all available from Cognis Corporation. These products are all mixtures of alkyl mono- and oligoglucopyranosides with alkyl groups based on fatty alcohols derived from coconut and/or palm kernel oil. Glucopon 220, 225 and 425 are examples of particularly suitable alkyl polyglycosides. Glucopon 220 is an alkyl polyglycoside which contains an average of 1.4 glucosyl residues per molecule and a mixture of 8 and 10 carbon alkyl groups (average carbons per alkyl chain—9.1). Glucopon 225 is a related alkyl polyglycoside with linear alkyl groups having 8 or 10 carbon atoms (average alkyl chain—9.1 carbon atoms) in the alkyl chain. Glucopon 425 includes a mixture of alkyl polyglycosides which individually include an alkyl group with 8, 10, 12, 14 or 16 carbon atoms (average alkyl chain—10.3 carbon atoms). Glucopon 600 includes a mixture of alkyl polyglycosides which individually include an alkyl group with 12, 14 or 16 carbon atoms (average alkyl chain 12.8 carbon atoms). Glucopon 625 includes a mixture of alkyl polyglycosides which individually include an alkyl group having 12, 14 or 18 carbon atoms (average alkyl chain 12.8 carbon atoms). Another example of a suitable commercially available alkyl polyglycoside is TL 2141, a Glucopon 220 analog available from ICI. BASF Corporation offers MASIL silicones that are modified to contain alkyl, polyglycol, amino groups, which may be included in the hydrogel precursor composition. For instance, MASIL SF-19 is a modified silicone glycol.

The hydrogel composition may be used in sheet form as the absorbent gel composition 121 of the absorbent article 100 illustrated in FIGS. 1-3 or as the material of the absorbent core 122 of the absorbent article 100 illustrated in FIGS. 4 and 5. The hydrogel composition may also be in particulate form when used as the absorbent core 122 of the absorbent article 100 illustrated in FIGS. 4 and 5. In one embodiment, the hydrogel composition 121 includes an adhesive gel composition with hydrogel particulate mixed therein.

The hydrogel composition may be intertwined into a fibrous web to enhance the mechanical properties of the hydrogel as described in U.S. patent application Ser. No. 11/513,831, which is incorporated herein for all relevant and consistent purposes. The web may act as a scaffold or support matrix that enhances the rigidity of the skin-adhesive and absorbent gel composition, especially under wet conditions. Also, the web can provide a fiber structure, pore size, and pore distribution that achieves a tailored handling of aqueous fluids. For example, a meltblown web, which has a relatively small pore size, is useful for wicking away and distributing an aqueous fluid over a large area, while a bonded carded web is useful for applications when high fluid holding capacity is desired. Fluid handling capacity can be controlled by the relative hydrogel content in the hydrogel-fibrous web composite.

The hydrogel polymer may be integral with the fibers of the web. For example, the hydrogel polymer may be intertwined with the fibers of the webs. As such, the hydrogel polymer cannot be easily separated from the web and is effectively a permanent part of the structure of the web. Thus, the hydrogel allows the web to absorb water or moisture (including water vapor) to a much greater extent than the web alone. For instance, in one embodiment, the hydrogel polymer is integrated into a hydrophobic fibrous web that would not otherwise absorb any substantial amount of water or moisture, changing a relatively hydrophobic web to be water and moisture absorbent.

In some embodiments, the hydrogel extends through the thickness of the web. For example, the hydrogel may extend beyond the thickness of the web. As such, the thickness of the web will be smaller than the thickness of the hydrogel. Without wishing to be bound by any particular theory, it is believed that the skin-adhesive and absorption ability of the hydrogel-fibrous web composite can be enhanced by having the hydrogel extend beyond the thickness of the web, such that the exposed outer layer of the composite is primarily the hydrogel.

In order to integrate the hydrogel polymer into the fibrous web, the hydrogel precursor composition described above is allowed to saturate the fibrous web before the composition is cured. The hydrogel polymer is then polymerized from monomers that have been saturated and impregnated within the fibrous web. Upon polymerization, the resulting hydrogel polymer forms within the fibrous web, effectively integrating the hydrogel polymer within the fibers of the web. For instance, the hydrogel polymer may be intertwined with the fibers of the web. Also, the hydrogel polymer typically crosslinks with itself to form a three-dimensional polymer network that is integral to and intertwined with the fibers of the web. As such, the hydrogel polymer network is physically integrated within the web and cannot be easily separated from the fibers of the web.

In some embodiments, depending upon the nature of the fibers of the web, the type of hydrogel polymer used, and the energy source used to initiate polymerization, the hydrogel polymer may also have additional chemical bonds or forces further attracting the hydrogel to the fibers of the web. For instance, the hydrogel polymer may crosslink with the fibers of the web, forming covalent bonds with the fibers of the web. In other embodiments, other chemical forces, such as van-der-Waals forces, hydrogen bonding, ionic bonding, etc., further integrate the hydrogel polymer to the fibers of the web.

The amount of hydrogel integrated into the fibrous web can be controlled by the amount of hydrogel monomer present in the hydrogel precursor composition. As such, controlling the amount of hydrogel in the composite web allows for control of the skin-adhesion properties of the composite web and the amount of water or moisture that can be absorbed by the composite web. Depending on the intended use of the hydrogel-fibrous web composite, the hydrogel can be present in the hydrogel-fibrous web composite at relatively high ratios. In some embodiments, the ratio of hydrogel to the fibrous web is at least about 10:1, at least about 15:1, at least about 30:1, at least about 50:1 or even at least about 100:1. In other embodiments the ratio of hydrogel to the fibrous web is from about 1:1 to about 100:1, from about 5:1 to about 100:1, from about 10:1 to about 100:1 or even from about 30:1 to about 100:1.

Expressed in terms of basis weight, in some embodiments the hydrogel is present in the hydrogel-fibrous web composite at basis weights of from about 10 g/m$^2$ to about 1000 g/m$^2$, from about 50 g/m$^2$ to about 900 g/m$^2$, from about 100 g/m$^2$ to about 800 g/m$^2$, from about 200 g/m$^2$ to about 700 g/m$^2$, or even from about 300 g/m$^2$ to about 600 g/m$^2$.

The location of the hydrogel integrated within the web may be somewhat controlled by the wettability and structure of the web and the manner of application of the hydrogel precursor composition to the web. For instance, application of the hydrogel precursor composition to only one side of the web, and subsequent polymerization, can result in the hydrogel polymer being present mainly in that side of the web. Viscosity modifiers may also be added to increase the viscosity of the hydrogel precursor composition to allow for controlled placement and formation of the hydrogel following polymerization.

As one skilled in the art will recognize, any method of saturating and/or impregnating the hydrogel precursor composition into the web may be used. For example, the hydrogel precursor formulation may be applied to the fibrous web using any conventional technique, such as bar, roll, knife, curtain, foam, print (e.g., rotogravure), slot-die, drop-coating, or dip-coating techniques. For instance, the hydrogel precursor composition may be applied topically to the external surfaces of the fibrous web. In one particular embodiment, the hydrogel precursor composition is applied uniformly to one or both surfaces of the fibrous web.

In one embodiment, the fibrous web is passed over a guide roll and into a bath with the treatment time controlled by first and second guide rolls located within the bath. The nip between first and second squeeze rolls downstream of the bath removes any excess hydrogel precursor composition which may be returned to the bath.

In other application techniques, where one desires to treat only a single side, and not the inner layers or opposing side of the fibrous web, other processes can be used, such as rotary screen, reverse roll, Meyer-rod, Gravure, slot-die, gap-coating, etc. However, even according to these application techniques, a sufficient amount of the hydrogel precursor composition penetrates the web, allowing the hydrogel to be integral to the fibers upon polymerization.

Regardless of the method of impregnation or saturation of the web, the hydrogel monomers saturated and/or impregnated within the web may be polymerized, either before or after drying of the web, depending on the polymerization initiation method. For instance, when a UV-initiator is present in the hydrogel precursor composition to initiate the polymerization of the hydrogel monomers upon the application of UV radiation, the web may be passed under a UV lamp (not shown) for a specific time allowing for the desired degree of polymerization, prior to drying the web. Then the web may be further dried, if needed, by passing over dryer cans or other drying means and then wound between two release film or paper layers as a roll or converted to the use for which it is intended. Alternative drying means include ovens, through air dryers, infra red dryers, air blowers, and the like.

Drying the hydrogel-fibrous web composite can control the water content of the composite, which can affect the amount of water that the hydrogel can absorb. In most applications, the water content of the hydrogel in the hydrogel-fibrous web composite will be relatively low, which allows for more water and moisture to be absorbed by the hydrogel. In one embodiment, the water content of the hydrogel in the hydrogel-fibrous web composite is less than about 20% by weight and, in another embodiment, less than about 15% by weight. In other embodiments, the water content of the hydrogel in the hydrogel-fibrous web composite will be less than about 10% by weight, less than about 5% by weight or even less than 2% by weight.

For example, the fibrous web may pass over a guide roll from a fibrous web supply roll. The fibrous web is first impregnated or saturated with the hydrogel precursor composition in a treatment center. Then, the treated fibrous web may be combined with a first release layer supplied from a release layer supply roll. The treated fibrous web is then cured in a curing station, such as, for example, by UV radiation. The fibrous web may then be dried in a dryer, and combined with a second release layer supplied from a release layer supply roll. Finally, the treated fibrous web sandwiched between the first release layer and the second release layer can then be rewound on a roll.

It is also understood that the method of treatment of the fibrous web with the impregnating hydrogel precursor composition may also incorporate other ingredients into the web such as the skin benefit agents described below. These other additives may be included either before or after a curing step. For instance, in some embodiments, the skin benefit agent may be present in the hydrogel precursor composition, which can help the additive become impregnated within the resulting hydrogel-fibrous web composite.

The hydrogel can be integrated into any suitable fibrous web, including both woven and nonwoven webs. In general, the intended end use of the composite web will dictate the composition and type of web utilized. In one particular embodiment, the fibrous web is a porous fibrous web. In this embodiment, the porosity of the fibrous web allows the hydrogel to penetrate the pores of the web and for greater fluid transport of water and moisture into the web, facilitating the ability of the integrated hydrogel to absorb the water and moisture. Also, in those applications where comfort and breathability is desired, the porous fibrous web can be breathable, allowing air to flow through the web, while moisture and water are retained within the web. In other embodiments, porous films and foams can also be used in similar fashion as porous webs.

The nonwoven web may be a spunbond web, a meltblown web, a bonded carded web, or another type of nonwoven web, including natural and/or synthetic fibers, and may be present in a single layer or a multilayer composite including one or more nonwoven web layers. When constructed of synthetic polymers, a wide variety of thermoplastic polymers may be used to construct the nonwoven substrate, including without limitation polyamides, polyesters, polyolefins, copolymers of ethylene and propylene, copolymers of ethylene or propylene with a $C_4$-$C_{20}$ α-olefin, terpolymers of ethylene with propylene and a $C_4$-$C_{20}$ α-olefin, ethylene vinyl acetate copolymers, propylene vinyl acetate copolymers, styrene-poly(ethylene-α-olefin) elastomers, polyurethanes, A-B block copolymers where A is formed of poly (vinyl arene) moieties such as polystyrene and B is an elastomeric midblock such as a conjugated diene or lower alkene, polyethers, polyether esters, polyacrylates, ethylene alkyl acrylates, polyisobutylene, polybutadiene, isobutylene-isoprene copolymers, and combinations of any of the foregoing. In some particular embodiments, polyolefins, such as polyethylene and polypropylene homopolymers and copolymers, may be used to construct the nonwoven web. The webs may also be constructed of bicomponent or biconstituent filaments or fibers. The nonwoven webs may have a wide variety of basis weights, preferably ranging from about 8 g/m² to about 120 g/m².

Particularly suitable nonwoven webs can be hydrophobic webs, such as those including polyolefin fibers and polyester fibers. Meltblown and spunbond webs of polyolefin fibers such as, for example, polypropylene and polyethylene, may be integrated with hydrogel polymers to change the otherwise hydrophobic web to a water absorbent web, without substantially affecting the other properties of the web.

The type of nonwoven web can dictate the function of the resulting composite hydrogel-fibrous web. For example, a meltblown web, which has relatively small pore size, is useful for wicking away and distributing an aqueous fluid over a large area, while a bonded carded web is useful for applications when high fluid holding capacity is desired. Fluid handling capacity can be controlled by the relative hydrogel content in the hydrogel-fibrous web composite.

In some embodiments, the nonwoven web can be a composite nonwoven web, including but not limited to, coform webs, webs entangled with pulp fibers, etc. For instance, a suitable nonwoven composite web can be a polypropylene web entangled with pulp fibers, such as the fabric sold under the name HYDROKNIT by Kimberly-Clark Corp., Inc. of Neenah, Wis.

In another embodiment, the web can be a woven web. For instance, certain applications will typically involve woven webs of cotton, polyester, nylon, wool, and the like, and combinations thereof. For example, in some clothing applications, the fibrous web can be a woven web.

Additionally, the hydrogel-fibrous web composite can be combined with other webs to form a laminate. For instance, the hydrogel-fibrous web composite can be one or more layers of a spunbond-meltblown-spunbond (SMS) web.

Skin-Adhesive and Absorbent Aerogel Compositions

In one embodiment, the absorbent article 100 of FIGS. 1-3 contains a skin-adhesive and absorbent gel composition 121 comprising an aerogel. Further, the material of the absorbent core of the article 100 illustrated in FIGS. 4 and 5 may be an aerogel. Suitable aerogels include inorganic, organic and carbon aerogels. Aerogels may be produced by polycondensation reactions or "sol-gel processes."

Inorganic aerogels can be obtained by supercritical drying of highly cross-linked and transparent hydrogels synthesized by polycondensation of metal alkoxides. Silica aerogels are the most well known inorganic aerogels. Silica-based inorganic aerogels are typically derived using precursors or monomers such as tetramethyl orthosilicate (TMOS, $Si(OCH_3)_4$), tetraethyl orthosilicate (TEOS, $Si(OCH_2CH_3)_4$), combinations of the foregoing orthosilicates, or the like. Inorganic aerogels may be produced according to the methods described in U.S. Pat. No. 6,670,402 and inorganic silica aerogels may be produced by the methods of U.S. Pat. No. 7,265,158, both of which are incorporated herein by reference for all relevant and consistent purposes.

Organic aerogels may be synthesized by supercritical drying of the gels obtained by the sol-gel polycondensation reaction of monomers such as, for example, resorcinol with formaldehyde, in aqueous solutions. Carbon aerogels can be obtained by pyrolyzing the organic aerogels at elevated temperatures. Methods for producing organic aerogels and carbon aerogels are described in U.S. Pat. No. 7,378,450, which is incorporated herein by reference for all relevant and consistent purposes.

Organic aerogels may be produced by the reaction of any one or a combination of various monomers in an appropriate ratio with formaldehyde, furfural, or the like in the presence of a catalyst via a polymerization reaction (e.g., a polycondensation reaction). The monomer(s) is preferably a polyhydroxybenzene compound, exemplary embodiments of which include, for example, resorcinol, phenol, catechol, chloroglucinal, combinations thereof, and the like. Reaction of such monomers with formaldehyde or furfural generally produce, for example, resorcinol-furfural, resorcinol-formaldehyde, phenol-resorcinol-formaldehyde, catechol-formaldehyde, chloroglucinol-formaldehyde, or the like.

In one exemplary polymerization reaction to form an organic aerogel, the reactants (i.e., the monomers) are mixed with the catalyst to produce the aerogel in the form of a monolithic gel, which is then dried by solvent exchange and extraction. The resulting organic aerogel may then be pyrolized in an inert atmosphere (e.g., nitrogen) to form a carbon aerogel. More specifically, the polymerization reaction is a sol-gel polymerization of multifunctional organic monomers in a solvent (e.g., water). The sol-gel polymerization leads to the formation of highly cross-linked, transparent or translucent gels ("hydrogel sols"). A metal may also be added with the monomers; thereby forming an aerogel/metallic composite.

In a preferred sol-gel polymerization, one mole of resorcinol (1,3-dihydroxybenzene) condenses in the presence of a basic catalyst with two moles of formaldehyde. A mildly basic catalyst (e.g., sodium carbonate) is preferred. Resorcinol is a trifunctional monomer capable of receiving formaldehyde molecules in the 2-, 4-, and/or 6-positions on its ring. The substituted resorcinol rings condense with each other to form nanometer-sized clusters in solution. Eventually, the clusters crosslink through their surface groups (e.g., —$CH_2OH$) to form the hydrogel sol.

The size of the clusters may be regulated by the concentration of catalyst in the resorcinol-formaldehyde (RF) mixture. More specifically, the mole ratio of resorcinol (R) to catalyst (C) (R/C) controls the surface area and electrochemical properties of the resulting gel. Preferably, the R/C ratio is about 50 to about 300. Other commonly referenced ratios include resorcinol (R) to formaldehyde (F) (R/F) and resorcinol (R) to water (W) (R/W). Typically, the R/F and R/W molar ratios are each about 0.01 to about 10.

The hydrogel sol is then cured for a time and temperature sufficient to stabilize the aerogel structure and form a cured hydrogel. Curing times range from about 2 hours to about 5 days or more. Curing temperatures range from about 25 degrees centigrade (C.) to about 150° C. Pressures greater than 1 atmosphere (atm) can be used to decrease the curing time. After curing, RF aerogels may be translucent and dark red or black in color or substantially transparent.

The next step in organic aerogel preparation is to dry the cured hydrogel. If the polymerization solvent is removed from the gel by simple evaporation, large capillary forces are exerted on the pores, thereby forming a collapsed structure, i.e., a xerogel. In order to preserve the gel skeleton and minimize shrinkage, it is preferable to perform the drying step under supercritical conditions (described hereinafter). Other drying steps may also be conducted, if desired, usually before the supercritical extraction step. For example a solvent exchange may be conducted in which the cured hydrogel is contacted with an exchange solvent, e.g., acetone, prior to subjecting the cured hydrogel to supercritical extraction to form the dried aerogel. The supercritical extraction may be performed with a supercritical fluid, such as liquid carbon dioxide. Also, as an alternative or in addition to the exchange step, surfactants may be used to remove water from the cured hydrogel. The highly porous material obtained from this removal operation is the organic aerogel. By appropriate adjustment of drying conditions, a hybrid structure having characteristics of both a xerogel and an aerogel may be produced. For example, such a hybrid may be produced as a result of a partial evaporation of the gel solvent under conditions promoting xerogel formation followed by evaporation of the remaining solvent under conditions promoting aerogel formation. The resulting hybrid structure would then be dried under supercritical conditions and pyrolized. Preparation of other xerogel-aerogel hybrids may be produced by first evaporating under conditions promoting aerogel formation and completing the evaporation under xerogel-promoting conditions.

As noted above, one means for removing water from the cured hydrogel is by extraction under supercritical conditions. As used herein, a "supercritical fluid" (synonymously "supercritical solution" or "supercritical solvent") is one in which the temperature and pressure of the fluid are greater than the respective critical temperature and pressure of the fluid. A supercritical condition for a particular fluid refers to a condition in which the temperature and pressure are both respectively greater than the critical temperature and critical pressure of the particular fluid.

A "near-supercritical fluid" is one in which the reduced temperature (actual temperature measured in Kelvin divided by the critical temperature of the solution (or solvent) measured in Kelvin) and reduced pressure (actual pressure divided by critical pressure of the fluid) of the fluid are both greater than 0.8 but the fluid is not a supercritical fluid. A near-supercritical condition for a particular fluid refers to a condition in which the reduced temperature and reduced pressure are both respectively greater 0.8 but the condition is not supercritical. Under ambient conditions, the fluid can be a gas or a liquid. The term fluid is also meant to include a mixture of two or more different individual fluid. As used herein, the term "supercritical fluid" and "supercritical conditions" are intended to include near-supercritical fluids and near-supercritical conditions respectively.

The temperature and pressure of the extraction process depend on the choice of supercritical fluid. Generally, the temperature is less than about 250° C. and often less than about 100° C., while the pressure is about 50 atm to about 500 atm.

Solvents that can be used as supercritical fluids are sometimes referred to as dense gases. Suitable solvents for use as supercritical fluids include, for example, carbon dioxide, ethane, propane, butane, pentane, dimethyl ether, ethanol, water and mixtures thereof. Carbon dioxide is a preferred supercritical fluid for use in accordance with the present invention. For example, at 333 Kelvin (K) and 150 atm, the density of $CO_2$ is 0.60 g/cm$^3$; therefore, with respect to $CO_2$, the reduced temperature is 1.09, the reduced pressure is 2.06, and the reduced density is 1.28. Carbon dioxide is a particularly good choice of supercritical fluid. Its critical temperature (31.1° C.) is close to ambient temperature and thus allows the use of moderate process temperatures (less than about 80° C.). The time required for supercritical drying depends on the thickness of the gel.

In cases where the cured hydrogels are of sufficiently high density, such as greater than about 40 weight percent (wt %) solids, the pore network may have sufficient inherent strength to withstand the drying process without resort to supercritical drying conditions. Thus, carbon dioxide may be bled from the vessel under non-supercritical conditions. Non-supercritical drying is particularly attractive because of its reduced processing time. To maximize crosslinking and further increase the density of the gels, the cured hydrogel may be subjected to a cure cycle.

Following the solvent exchange/extraction step and any cure cycle, the organic aerogel may be pyrolized at elevated temperatures of about 400° C. to about 2,000° C. in an inert atmosphere of nitrogen, argon, neon, helium, or any combination of the foregoing gases to form a pyrolized aerogel, e.g., a carbon aerogel. The pyrolysis temperatures can alter the surface area and structure of the pyrolized aerogel. In particular, higher surface areas are achieved at lower temperatures. The resulting aerogels, independent of the procedure by which they are pyrolized, are black and not transparent due to the visible absorption properties of the carbon matrix.

The aerogels of the present disclosure typically have a surface area of from about 400 $m^2/g$ to about 2,000 $m^2/g$, a pore volume of about 0.5 $cm^3/g$ to about 10 $cm^3/g$, and a density of about 0.01 $g/cm^3$ to about 2.0 $g/cm^3$. Such properties can be readily determined by those skilled in the art. For example, surface area and pore volume can be determined by the BET method (the Brunauer, Emmett, and Teller method), and density can be determined by using a pycnometer.

Binders and/or fiber particles may be incorporated into the aerogel to produce a more mechanically stable aerogel as described in U.S. Pat. No. 6,887,563, which is incorporated herein by reference for all relevant and consistent purposes.

The aerogels may generally be utilized similar to the utilization of hydrogels as described above. Particularly, the aerogels may possess the same skin-adhesive and absorption properties and may include the same surfactants, adhesion modifiers and/or skin benefit agents described below.

Adhesion Modifiers

In accordance with the present disclosure, an adhesion modifier as disclosed in U.S. application Ser. No. 12/267,806 may suitably be included in the gel composition 121 and/or the perforated liner 123. The adhesion modifier may further allow the gel composition 121 and/or liner 123 to maintain its bonding strength with the substrate, yet remain gentle on the skin's surface. It should be understood that an adhesion modifier is optional and need be included in the absorbent article. The adhesion modifier may also behave as a delivery vehicle or carrier that can aid in delivering one or more skin benefit agents to the skin of a user. For example, in one embodiment, the adhesion modifier is in the form of a matrix. The matrix-like adhesion modifier may include (i.e., be filled with) at least one skin benefit agent as described below to function as a carrier for the skin benefit agent. The skin benefit agent-containing matrix may be dispersed within the gel composition.

Generally, the matrix-like adhesive modifiers are channel-like matrices or pore-like matrices. Specifically, the matrix is formed in the modifiers to contain "channels" or "pores" in which the skin benefit agents can be introduced. These types of adhesive modifiers serve a dual purpose of: (1) modifying the adhesion of the skin-adhesive and absorbent gel composition to the skin so that it can be adhered efficiently, but capable of releasing from the skin without damage to the skin; and (2) allowing for a controlled release of the skin benefit agents to the skin of the user.

It should be understood that while numerous delivery vehicles are known in the art, all delivery vehicles or carriers are not suitable for use in the skin-adhesive and absorbent gel compositions of the present disclosure. More particularly, the adhesion modifiers must be compatible with the gel composition to maintain flexibility and adhesive strength of the composition without causing damage to the surface of the skin.

In one embodiment, the adhesion modifier(s) are added to the hydrogel precursor composition described above. During polymerization, the adhesion modifier becomes suspended within the gel composition.

Suitable adhesion modifiers include, for example, colloidal particles, crosslinked copolymers, and combinations thereof. More particularly, colloidal particles well suited for use in the present disclosure include microcrystalline cellulose, fumed silica, silica, hydrated silica, and combinations thereof. Commercially available colloidal particles such as fumed silica (available as Cab-o-sil M5 from Cabot Corporation, Tuscola, Ill.) and blends of microcrystalline cellulose and cellulose gum (available as AVICEL 591 from FMC Corporation, Philadelphia, Pa.) are particularly suitable for use as adhesion modifiers.

In one particularly embodiment, the adhesion modifier may include polymer-like network or matrix structure, such as cross-linked cross polymers (for example, acrylate copolymers). Cross-linked acrylate crosspolymers well-suited for use in the present disclosure include allyl methacrylates crosspolymer, allyl methacrylate/glycol dimethacrylate crosspolymer, lauryl methacrylate/glycol dimethacrylate crosspolymer and derivatives thereof. Suitable examples include POLY-PORE E-200, POLY-PORE L-200, POLY-TRAP 7603 and POLYTRAP 6603 Adsorber which are all available from Amcol Health & Beauty Solutions (Arlington, Ill.). The POLY-PORE and POLYTRAP ingredients can be loaded with skin beneficial ingredients prior to inclusion in the skin-adhesive combination or are available pre-loaded from Amcol Health & Beauty Solutions as POLYTRAP 6035 Cyclomethicone, POLYTRAP 7100 Dimethicone Macrobeads, POLYTRAP 6500 Dimethicone/Petrolatum Powder, POLYTRAP 665TO (which is loaded with tocopherol), and POLYTRAP 6038 Mineral Oil Macrobeads.

In one embodiment, the skin-adhesive and absorbent composition includes from about 1% (by total weight composition) to about 50% (by total weight composition) adhesion modifier and, in other embodiments, from about 2% (by total weight composition) to about 25% (by total weight composition) or from about 5% (by total weight composition) to about 20% (by total weight composition) adhesion modifier.

Skin Benefit Agents

In accordance with the present disclosure, skin benefit agents may suitably be included in the gel composition 121, the absorbent core 122 and/or the perforated liner 123. A skin benefit agent generally provides a skin benefit (e.g., functional, aesthetic, or heath benefit) to the user/wearer. For example, a skin benefit agent such as an antiperspirant can be beneficial to the skin-adhesive and absorbent gel composition as it will prevent the gel composition from weakening as a result of increased sweating in specific areas of the body for use with the skin-adhesive composition.

Exemplary skin benefit agents may include for example: antiperspirants, deodorants, skin moisturizers, humectants, pH modulators, soothing agents, antimicrobials, preservatives, film formers, and combinations thereof. Antiperspirant agents are those active ingredients generally found in antiperspirant products. In the Final Rule for U.S. Antiperspirant Drug Products for Over-the Counter Human Use; Final Monograph (68 Federal Register 34273-34293, Jun. 9, 2003) an "antiperspirant" refers to a drug product applied topically that reduces the production of perspiration (sweat) at that site. See 21 CFR 350.3 for definition and 21 CFR 350.10 for a listing of the U.S. Antiperspirant active ingredients. The following is a list of ingredients currently listed in the INCI Dictionary under this category: adipic acid/ neopentyl glycol crosspolymer, aluminum chloride, aluminum chlorohydrate, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate (aluminum sulfate buffered), aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium tetrachlorohydrex GLY, aluminum zirconium trichlorohydrate, aluminum zirconium trichlorohydrex GLY, *Bursera Graveolens* fruit oil, ferric chloride, *Humulus Lupulus* (Hops) cone extract, *Hypericum Perforatum* flower/twig extract, zirconium powder, and combinations thereof. Particularly preferred antiperspirants for use in the skin-adhesive composition of the present disclosure include commercially available REACH Aluminum-Zirconium Complex (AZP) 908, and REACH 103, which is a chlorohydrate, both of which are commercially available from Reheis, Inc., Berkeley Heights, N.J.

Deodorants are agents that reduce or eliminate unpleasant odors and protect against the formation of malodor on bodily surfaces. Absorbents can act as deodorants if they have the ability to absorb malodorous chemicals. Also, chemical reactions can be used to destroy the malodorous substance in selected cases. Perfumes and the like can be used to mask the perception of malodor by the process of reodorization. Unpleasant odors also may be the result of microbiological activity. Thus, cosmetic biocides are ingredients frequently used in skin-surface deodorants. The following listing of deodorants is limited to those ingredients commonly used for this purpose: adipic acid/neopentyl glycol crosspolymer, Alpinia Uraiensis stalk/leaf water, aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum lactate, aluminum phenolsulfonate, aluminum sesquichlorohydrate, aluminum sesquichlorohydrex PEG, aluminum sesquichlorohydrex PG, aluminum sulfate, aluminum triphosphate, aluminum zinc oxide, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium tetrachlorohydrex GLY, aluminum zirconium tetrachlorohydrex PEG, aluminum zirconium tetrachlorohydrex PG, aluminum zirconium trichlorohydrate, aluminum zirconium trichlorohydrex GLY, amber powder, ammonium phenolsulfonate, ammonium silver zinc aluminum silicate, benzalkonium bromide, benzalkonium cetyl phosphate, benzalkonium chloride, benzalkonium saccharinate, benzethonium chloride, *Boesenbergia Pandurata* Rhizome extract, bromochlorophene, t-Butyl methylphenoxy phenol, calcium magnesium silicate, *Callicarpa Macrophylla* flower extract, *Candida Bombicola*/glucose/methyl rapeseedate ferment, capryloyl gold of pleasure amino acids, cetylpyridinium chloride, chlorophyllin-copper complex, chlorothymol, chloroxylenol, *Citrus Reticulata* (Tangerine) peel oil, cloflucarban, colloidal platinum, *Cuminum Cyminum* seed extract, *Curcuma Heyneana* root powder, cyclopentadecanone, dequalinium chloride, dichlorophene, dichloro-m-xylenol, dimethicone/PEG-15 crosspolymer, dipotassium capryloyl glutamate, disodium capryloyl glutamate, disodium dihydroxyethyl sulfosuccinylundecylenate, domiphen bromide, ethylhexylglycerin, fermented vegetable, hexachlorophene, hydrolyzed *Sasa Veitchii* extract, ketoglutaric acid, lauryl isoquinolinium bromide, laurylpyridinium chloride, magnesium/aluminum/zinc/hydroxide/carbonate, mentha aquatica water, methylbenzethonium chloride, methyl undecylenate, *Michelia Champaca* flower oil, micrococcus/hydrolyzed nonfat milk ferment, octadecenedioic acid, oligopeptide-10, *Pandanus Amaryllifolius* leaf extract, *Pelargonium Graveolens* water, phenol, *Phyllostachys Edulis* stem extract, *Piper Betle* leaf oil, polyaminopropyl biguanide stearate, potassium capryloyl glutamate, *Rosmarinus Officinalis* (Rosemary) flower extract, saccharomyces/persimmon fruit juice ferment extract, *Saccharomyces/Rhodobacter/Lactobacillus/Leuconostoc/Streptomyces/Griseus/Aspergillus/Bacillus* ferment filtrate, *Sasa Senanensis* leaf extract, *Sasa Senanensis* leaf powder, silver copper zeolite, sodium bicarbonate, sodium capryloyl glutamate, sodium phenolsulfonate, sodium silver aluminum silicate, *Stemmacantha Carthamoides* root extract, totarol, triclocarban, triclosan, tricyclodecenyl propionate, *Urginea Maritima* tuber extract, zeolite, zinc lactate, zinc phenolsulfonate, zinc ricinoleate, zinc silicate, and combinations thereof.

Humectants are hydroscopic agents that are widely used as skin moisturizers. Their function is to prevent the loss of moisture from the skin and to attract moisture from the environment. Common humectants include, for example, glycerin, butylene glycol, betaine, sodium hyaluronate, and the like, and combinations thereof.

Soothing agents, also referred to as emollients, lubricate, sooth, and soften the skin surface. Exemplary emollients include oily or waxy ingredients such as esters, ethers, fatty alcohols, hydrocarbons, silicones, and the like, and combinations thereof.

Film formers, also referred to as skin barrier enhancers or occlusive materials, increase the water content of the skin by blocking water evaporation. These materials generally include lipids which tend to remain on the skin surface or hydrocarbons such as petrolatum and wax.

Rheology enhancers may help increase the melt point viscosity of the formulation so that the formulation readily remains on the surface of the substrate and/or laminated article and does not substantially migrate into the interior of the substrate, while substantially not affecting the transfer of the formulation to the skin. The rheology enhancers help the formulation to maintain a high viscosity at elevated temperatures, such as those encountered during storage and transportation. Additionally, rheology enhancers can influence the overall consistency and skin feel of the formulation.

Suitable rheology enhancers include combinations of alpha-olefins and styrene alone or in combination with mineral oil or petrolatum, combinations of di-functional α-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology enhancers. Other suitable examples of oil-soluble rheology enhancers include, but are not limited to, aluminum stearate, aluminum tristearate, arachidyl alcohol, arachidyl behenate, behenyl alcohol, $C_{8-22}$ alkyl acrylate/butyl dimethicone methacrylate copolymer, $C_{12-22}$ alkyl acrylate/hydroxyethylacrylate copolymer, $C_{18-38}$ alkyl, $C_{24-54}$ acid ester, $C_{20-24}$ alkyl dimethicone, $C_{24-28}$ alkyl dimethicone, $C_{30-60}$ alkyl dimethicone ceresin, cerotic acid, cetearyl alcohol, cetearyl dimethicone/vinyl dimethicone crosspolymer, cetyl alcohol, cetyl glycol, dibehenyl fumarate, hydrogenated polyisobutene, hydrogenated oils, isocetyl alcohol, isocetyl stearoyl stearate, isophthalic acid/pentaerythritol crosspolymer benzoate/isostearate, isostearyl alcohol, isostearyl stearoyl stearate, jojoba alcohol, lanolin alcohol, lanolin wax, neopentyl glycol dicaprate, neopentyl glycol dicaprylate/dicaprate, neopentyl glycol dicaprylate/dipelargonate/dicaprate, neopentyl glycol diethylhexanoate, neopentyl glycol diheptanoate, neopentyl glycol diisostearate, neopentyl glycol dilaurate, ozokerite, palm alcohol, palm kernel alcohol, paraffin, pentaerythrityl tetramyristate, pentaerythrityl tetraoleate, pentaerythrityl tetrapelargonate, pentaerythrityl tetrastearate, pentaerythrityl trioleate, silica, synthetic beeswax, synthetic candelilla wax, synthetic carnauba, vinyldimethyl/trimethylsiloxysilicate, stearyl dimethicone crosspolymer VP/eicosene copolymer and VP/hexadecene copolymer. Water soluble or water dispersable rheology modifiers include, but are not limited to, acetamide MEA, acrylamide/ethalkonium chloride acrylate Copolymer, acrylamide/ethyltrimonium chloride acrylate/ethalkonium chloride acrylate copolymer, acrylamides copolymer, acrylamide/sodium acrylate copolymer, acrylates/acetoacetoxyethyl methacrylate copolymer, acrylates/beheneth-25 methacrylate copolymer, acrylates/$C_{10-30}$ alkyl acrylate crosspolymer, acrylates/ceteth-20 itaconate copolymer, acrylates/ceteth-20 methacrylate copolymer, acrylates/laureth-25 methacrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylates/vinyl neodecanoate crosspolymer, acrylic acid/acrylonitrogens copolymer, agar, agarose, algin, alginic acid, ammonium acryloyldimethyltaurate/vinyl formamide copolymer, ammonium acryloyldimethyltaurate/VP copolymer, ammonium alginate, ammonium chloride, amylopectin, avena sativa (oat) kernel flour, bentonite, calcium alginate, calcium carrageenan, $C_{20-40}$ alkyl stearate, carbomer, carboxybutyl chitosan, carboxymethyl hydroxyethylcellulose, carboxymethyl hydroxypropyl guar, cassia Gum, cellulose gum, cetyl hydroxyethylcellulose, $C_{12-14}$ hydroxyalkyl, hydroxyethyl sarcosine, cocamide DEA, cocamide MEA, decyl HDI/PEG-180 crosspolymer, decyltetradeceth-200 isostearate, dextrin, dimethicone/PEG-10 crosspolymer, dimethicone/PEG-15 crosspolymer, dimethylacrylamide/ethyltrimonium chloride methacrylate copolymer, disteareth-75 IPDI, disteareth-100 IPDI, gelatin, gellan gum, hectorite, hydrated silica, hydrolyzed cellulose gum, hydroxybutyl methylcellulose, hydroxyethylcellulose, hydroxyethyl ethylcellulose, hydroxypropyl chitosan, hydroxypropyl guar, hydroxypropyl methylcellulose, hydroxypropyl methylcellulose stearoxy ether, hydroxypropyl starch, hydroxypropyl starch phosphate, hydroxypropyl xanthan gum, isopolyglyceryl-3 dimethicone, isopolyglyceryl-3 dimethiconol, lauryl hydroxysultaine, lauryl/myristyl glycol hydroxypropyl ether, lauryl PEG-9 polydimethylsiloxyethyl dimethicone, lauryl polyglyceryl-3 polydimethylsiloxyethyl dimethicone, levan, magnesium alginate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, montmorillonite, myristamidopropyl hydroxysultaine, oatamidopropyl betaine, octacosanyl glycol isostearate, octadecene/MA copolymer, pectin, PEG-150/decyl alcohol/SMDI copolymer, PEG-175 diisostearate, PEG-190 distearate, PEG-15 glyceryl tristearate, PEG-140 glyceryl tristearate, PEG-240/HDI copolymer bis-decyltetradeceth-20 ether, PEG-100/IPDI copolymer, PEG-180/laureth-50/TMMG copolymer, PEG-10/lauryl dimethicone crosspolymer, PEG-15/lauryl dimethicone crosspolymer, PEG-2M, PEG-5M, PEG-7M, PEG-9M, PEG-14MPEG-20M, PEG-23M, PEG-25M, PEG-45M, PEG-65M, PEG-90M, PEG-115M, PEG-160M, PEG-180M, PEG-120 methyl glucose triisostearate, PEG-120 methyl glucose trioleate, PEG-150 pentaerythrityl tetrastearate, PEG/PPG-120/10 trimethylolpropane trioleate, PEG/PPG-120/10 trimethylpropane trioleatePEG-150/stearyl alcohol/SMDI copolymer, polyacrylate-3, polyacrylate-10, polyacrylate-11, polyacrylic acid, polycyclopentadiene, polyester-5, polyether-1, polyethylene/isopropyl maleate/MA copolyol, polyglycerin-20, polyglycerin-40, polyglyceryl-3 disiloxane dimethicone polyglyceryl-3 polydimethylsiloxyethyl dimethicone, polyquaternium-86, polyvinyl alcohol, potassium polyacrylate, potato starch modified, PVP montmorillonite, sodium acrylates/acrylonitrogens copolymer, sodium acrylates copolymer, sodium acrylates crosspolymer, sodium acrylate/sodium acrylamidomethylpropane sulfonate copolymer, sodium acrylate/sodium acryloyldimethyl taurate/acrylamide copolymer, sodium acrylates/vinyl isodecanoate crosspolymer, sodium acrylate/vinyl alcohol copolymer, sodium acryloyldimethyl taurate/acrylamide/VP copolymer, sodium carboxymethyl beta-glucan, sodium carboxymethyl starch, sodium carrageenan, sodium cellulose sulfate, sodium chloride, sodium hydroxypropyl starch phosphate, sodium isooctylene/MA copolymer, sodium polyacrylate, sodium silicoaluminate, sodium starch octenylsuccinate, sodium sulfate, steareth-100/PEG-136/HDI copolymer, tapioca starch, TEA-alginate, TEA-carbomer, trehalose hydroxypropyltrimonium chloride, tridecyl alcohol, undecyl alcohol, wheat germamidopropyl betaine, xanthan gum, yeast, polysaccharides, and *Zea Mays* (corn) starch.

Still other optional components that may be desirable for use in the skin-adhesive and absorbent gel composition include those cosmetic and pharmaceutical ingredients commonly used in the skin care industry. Examples include abrasives, absorbents, aesthetic components (fragrances, pigments, colorings/colorants), essential oils, skin sensates, astringents (e.g., clove oil, menthol, camphor, eucalyptus oil, eugenol, menthyl lactate, witch hazel distillate), anti-acne agents, anti-caking agents, antifoaming agents, antioxidants, binders, biological additives, buffering agents, bulking agents, chelating agents, chemical additives, colorants, cosmetic astringents, cosmetic biocides, denaturants, drug astringents, external analgesics, opacifying agents, propellants, reducing agents, sequestrants, skin bleaching and lightening agents (e.g., hydroquinone, kojic acid, ascorbic acid, magnesium ascorbyl phosphate, ascorbyl glucosamine), skin-moisturizing agents, skin-conditioning agents, skin soothing and/or healing agents (e.g., panthenol and derivatives thereof, aloe vera, pantothenic acid and derivatives thereof, allantoin, bisabolol, dipotassium glycyrrhizinate), hemorrhoid treating agents (e.g., witch hazel), prebiotics, probiotics, urinary tract infection treating agents, yeast infection treating agents, bacterial vaginosis treating agents, skin treating agents, sunscreens, thickeners, and vitamins, and combinations thereof. Examples of these and other agents are disclosed in The CTFA Cosmetic Ingredient Handbook, 12$^{th}$ Ed. (2007), which is hereby incorporated by reference to the extent that it is consistent herewith.

The amounts of the optional components will depend on the type of skin-adhesive and absorbent gel composition used and as well as the desired benefits of the optional components. In one embodiment, the gel composition includes from about 0.001% (by total weight composition) to about 60% (by total weight composition) skin benefit agent and, in another embodiment, from about 0.01% (by total weight composition) to about 30% (by total weight composition) skin benefit agent, and even from about 0.01% (by total weight composition) to about 20% (by total weight composition) skin benefit agent.

More than one skin benefit agent can be used depending on the desired effect(s) of the benefit agents.

The skin benefit agent may be homogeneously dispersed throughout the skin-adhesive and absorbent gel composition or may be located at discreet portions of the gel composition. For example, a skin benefit agent such as a humectant that functions as a skin moisturizer may be located at the peripheral portions of the gel composition that are more likely to contact the skin. Further, additives relating to vaginal ecology such as prebiotics, probiotics, pH balance agents, urinary tract infection treating agents, yeast infection treating agents and bacterial vaginosis treating agents and additives such as hemorrhoid treating agents could be located at the central portions of the gel composition. Alternatively or additionally, the skin benefit agent may be micro-embossed or printed on the surface of the gel composition. In some embodiments, the skin benefit agent is microencapsulated and dispersed throughout the gel composition.

Packaging

The absorbent article 100 may be individually packaged to maintain the desired moisture content of the gel composition. For example, the absorbent article 100 may be packaged in a hermetically sealed foil envelop similar to the packaging used for moist toilettes or "wet-naps." Other packaging materials include polyester or aluminized polyester.

The following description includes non-limiting examples of specific embodiments of absorbent articles that further illustrate the present disclosure.

EXAMPLES

Example 1: Two-Layered Absorbent Article

The absorbent article includes a substrate layer that may be a film, nonwoven, woven, netting or foam. A skin-adhesive and absorbent gel composition is attached to the body-facing surface of the substrate.

Example 2: Two-Layered Absorbent Article with a Contoured Fit

The absorbent article is constructed according to Example 1; however the skin-adhesive and absorbent gel composition is shaped and sized to match the contours of female genitalia. Particularly, the gel composition is generally dome shaped, i.e., it is thicker in its central portion and thinner in the peripheral portions.

Example 3: Two-Layered Absorbent Article with a Fibrous Web

The absorbent article includes a substrate as in Example 1. A skin-adhesive and absorbent gel composition is attached to the body-facing surface of the substrate. The gel composition includes a fibrous web with the threads of the web being coated by a hydrogel.

Example 4: Two-Layered Absorbent Article with Two Gel Layers

The substrate of the absorbent article is composed of a fluid-impermeable gel such as a fluid-impermeable silicone gel. A second gel composition that is skin-adhesive and absorbent is attached to the body-facing surface of the gel substrate. The substrate is thinner in the z-direction than the gel composition.

Example 5: Three-Layered Absorbent Article

The absorbent article includes a substrate as in Example 1. On the body-facing surface of the substrate is an absorbent core. The absorbent core may be composed of a hydrogel composition. A perforated liner made of a hydrophobic silicone gel is attached to the body-surface side of the absorbent core. The perforations of the liner may be in the form of apertures, slots, funnels or holes.

Example 6: Three-Layered Absorbent Article that Includes Hydrating Perforated Liner The absorbent article includes a substrate and absorbent core as in Example 5. The perforated liner of the absorbent article is a silicone gel that absorbs and draws away menstrual fluid but maintains hydration of the skin that contacts the liner. The perforated liner is sized and shaped to contact the labial region of the wearer.

Example 7: Three-Layered Absorbent Article that Includes Skin Benefit Agents

The absorbent article of Example 5 includes skin benefit agents. Particularly, the central portion of the absorbent core includes probiotics and pH balance agents for vaginal ecology and the peripheral portions of the absorbent core include a moisturizer to prevent skin irritation.

Example 8: Four-Layered Absorbent Article

The absorbent article includes a substrate layer as in Example 1 attached to the body-facing surface of the substrate is an absorbent core that contains an absorbent gel. Attached to the body-facing surface of the absorbent core is a fibrous web that is coated with a hydrogel that provides dimensional resilience (in the x, y and z direction) to prevent collapse of the absorbent article and loss of fluid capacity. A perforated liner made of a hydrophobic silicone gel is attached to the body-facing surface of the fibrous web. The perforated liner is comfortable to the wearer, i.e., in that it does not irritate the skin, and is malleable.

Having described the disclosure in detail, it will be apparent that modifications and variations are possible without departing from the scope of the disclosure defined in the appended claims.

In view of the above, it will be seen that the several objects of the disclosure are achieved and other advantageous results attained.

As various changes could be made in the above formulations and substrates/articles without departing from the scope of the disclosure, it is intended that all matter contained in the above description shall be interpreted as illustrative and not in a limiting sense.

What is claimed is:

1. An absorbent article comprising a fluid impermeable substrate having a body-facing surface and a garment-facing surface, the body-facing surface having a skin-adhesive and absorbent gel composition thereon for adhering the substrate directly to a wearer and for absorbing bodily fluids, the gel composition comprises a hydrogel composed of monomers selected from the group consisting of N-vinyl pyrrolidone, hydroxyethyl methacrylate, methacrylic acid or its salt, styrene sulfonic acid or its salt, potassium sulfopropyl acrylate, dimethyl acrylamide, dimethyl amino ethyl methacrylate or its quaternary salt derivative, acrylamido methyl propane sulfonic acid or its salt and mixtures thereof, wherein the gel composition further comprises an adhesion modifier dispersed within the gel composition, wherein the adhesion modifier is selected from allyl methacrylates crosspolymer, allyl methacrylate/glycol dimethacrylate crosspolymer, lauryl methacrylate/glycol dimethacrylate crosspolymer and derivatives thereof, wherein the hydrogel is intertwined with a fibrous web, and wherein the ratio of the hydrogel to the fibrous web is from about 30:1 to about 100:1 by basis weight.

2. The absorbent article as set forth in claim 1, wherein the skin-adhesive and absorbent gel composition includes from about 5% to about 20% by total weight of the composition adhesion modifier.

3. The absorbent article as set forth in claim 1, wherein the skin-adhesive and absorbent gel composition is capable of absorbing at least 20% of its weight in water.

4. The absorbent article as set forth in claim 1, wherein the skin-adhesive and absorbent gel composition is capable of absorbing at least 100% of its weight in water.

5. The absorbent article as set forth in claim 1, wherein the skin-adhesive and absorbent gel composition is capable of absorbing at least 1000% of its weight in water.

6. The absorbent article as set forth in claim 1, wherein the hydrogel is formed from a precursor composition comprising a monomer, initiator, a cross-linking agent and a solvent.

7. The absorbent article as set forth in claim 1, wherein the hydrogel has a three-dimensional cross-linked structure.

8. The absorbent article as set forth in claim 1, wherein the skin-adhesive and absorbent gel composition comprises a skin benefit agent, wherein the skin benefit agent is selected from the group consisting of antiperspirants, deodorants, skin moisturizers, humectants, pH modulators, soothing agents, antimicrobials, preservatives, film formers, and combinations thereof.

9. The absorbent article as set forth in claim 8, wherein the skin-adhesive and absorbent gel composition comprises from about 0.001% to about 60% by total weight of the composition of the skin benefit agent.

10. The absorbent article as set forth in claim 1, wherein the substrate is composed of a material selected from the group consisting of a polymeric film, polymeric foam, woven fabric, nonwoven fabric and knitted fabric.

11. The absorbent article as set forth in claim 1, wherein the skin-adhesive and absorbent gel composition defines a central portion and a peripheral portion wherein the peripheral portion is more adhesive to the skin of the wearer than the central portion.

12. The absorbent article as set forth in claim 11, wherein the central portion is more absorbent than the peripheral portion.

* * * * *